(12) United States Patent
King et al.

(10) Patent No.: US 8,304,477 B2
(45) Date of Patent: Nov. 6, 2012

(54) LIQUID OXYALKYLENE BRIDGED BIS- AND TRIS-PHOSPHITE ESTER MIXTURES

(75) Inventors: Roswell E. King, Pleasantville, NY (US); Stanley Padegimas, Mobile, AL (US); Marie A. McGregor, legal representative, Mobile, AL (US); Brian Bakke, Greensboro, NC (US); Lucas Moore, Marietta, GA (US); Sai P Shum, Monroe Township, NJ (US); Robert Cordova, Madison, WI (US)

(73) Assignee: BASF SE, Ludwigshafen (DE)

( * ) Notice: Subject to any disclaimer, the term of this patent is extended or adjusted under 35 U.S.C. 154(b) by 301 days.

(21) Appl. No.: 12/693,700

(22) Filed: Jan. 26, 2010

(65) Prior Publication Data
US 2010/0240810 A1 Sep. 23, 2010

Related U.S. Application Data

(63) Continuation of application No. 12/499,474, filed on Jul. 8, 2009, now abandoned.

(60) Provisional application No. 61/134,667, filed on Jul. 11, 2008.

(51) Int. Cl.
C08K 5/00 (2006.01)
C08K 5/51 (2006.01)
C08K 5/524 (2006.01)
C07F 9/145 (2006.01)
(52) U.S. Cl. .................. 524/151; 524/128; 524/150
(58) Field of Classification Search .......... 524/128, 524/150, 151
See application file for complete search history.

(56) References Cited

U.S. PATENT DOCUMENTS
5,322,871 A * 6/1994 Pitteloud et al. ............ 524/151
* cited by examiner

*Primary Examiner* — Mark Eashoo
*Assistant Examiner* — Angela C Scott
(74) *Attorney, Agent, or Firm* — Tyler A. Stevenson

(57) ABSTRACT

Disclosed are mixtures of oxyalkylene bridged bis- and tris-phosphite esters of formulae I and II

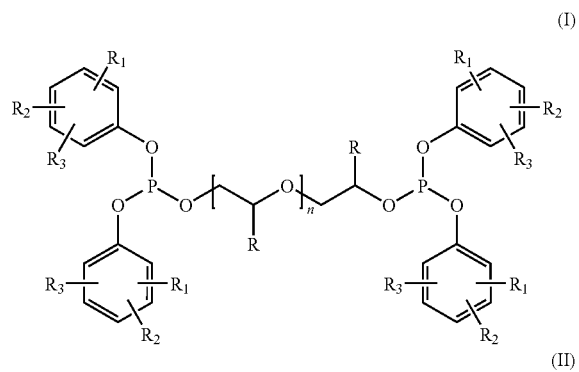

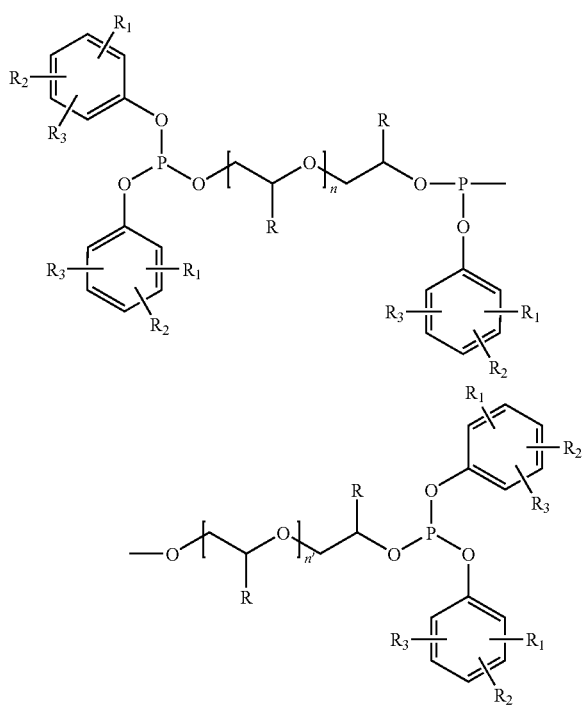

where R is hydrogen or methyl, n and n' are independently an integer from 1 to 45 and $R_1$, $R_2$ and $R_3$ are each independently hydrogen, straight or branched chain alkyl of 1 to 12 carbon atoms, phenylalkyl of 7 to 9 carbon atoms, phenylalkyl of 7 to 9 carbon atoms substituted on the phenyl ring by one to three straight or branched chain alkyl of 1 to 12 carbon atoms or $R_1$, $R_2$ and $R_3$ are each independently $-(CH_2)_k-COOR_4$ where k is 0, 1 or 2 and $R_4$ is hydrogen or straight or branched chain alkyl of 1 to 20 carbon atoms. The mixtures of formula I and II are liquid at ambient conditions and are effective stabilizers for polyolefins.

16 Claims, No Drawings

LIQUID OXYALKYLENE BRIDGED BIS- AND TRIS-PHOSPHITE ESTER MIXTURES

This application is a continuation of U.S. application Ser. No. 12/499,474, filed Jul. 8, 2009, abandoned, which claims benefit of U.S. provisional app. No. 61/134,667, filed Jul. 11, 2008, the contents of which are incorporated by reference.

The invention pertains to mixtures of oxyalkylene bridged bis- and tris-phosphites. The phosphite mixtures are liquid at ambient temperature and pressure. The phosphites and phosphite mixtures are useful for the stabilization of polyolefins.

BACKGROUND

Organic phosphorus compounds are well known polymer process stabilizers. For Example, Plastics Additives Handbook, 4$^{th}$ Ed., R. Gaechter, H. Mueller, Eds., 1993, pages 40-71, discusses the stabilization of polypropylene (PP) and polyethylene (PE).

Known phosphite and phosphonite stabilizers include for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, bis(2,4-di-α-cumylphenyl) pentaerythrtitol diphosphite, diisodecyl pentaerythritol diphosphite, bis(2,4-di-tert-butylphenyl) pentaerythritol diphosphite (D), bis(2,6-di-tert-butyl-4-methylphenyl) pentaerythritol diphosphite (E), bisisodecyloxy-pentaerythritol diphosphite, bis(2,4-di-tert-butyl-6-methylphenyl) pentaerythritol diphosphite, bis(2,4,6-tri-tert-butylphenyl) pentaerythritol diphosphite, tristearyl sorbitol triphosphite, tetrakis(2,4-di-tert-butylphenyl) 4,4'-biphenylene-diphosphonite (H), 6-isooctyloxy-2,4,8,10-tetra-tert-butyl-dibenzo[d,f][1,3,2]dioxaphosphepin (C), 6-fluoro-2,4,8,10-tetra-tert-butyl-12-methyl-dibenzo[d,g][1,3,2]dioxaphosphocin (A), bis(2,4-di-tert-butyl-6-methylphenyl) methyl phosphite, bis(2,4-di-tert-butyl-6-methylphenyl) ethyl phosphite (G), 2,2',2"-nitrilo[triethyltris(3,3'5,5'-tetra-tert-butyl-1,1'-biphenyl-2,2'-diyl)phosphite] (B), bis(2,4-di-t-butylphenyl) octylphosphite, poly(4,4'-{2,2'-dimethyl-5,5'-di-t-butylphenylsulfide-}octylphosphite), poly(4,4'{-isopropylidenediphenol}-octylphosphite), poly(4,4'-{isopropylidenebis[2,6-d]bromophenol}-octylphosphite), poly(4,4'-{2,2'-dimethyl-5,5'-di-t-butylphenylsulfide}-pentaerythrityl diphosphite),

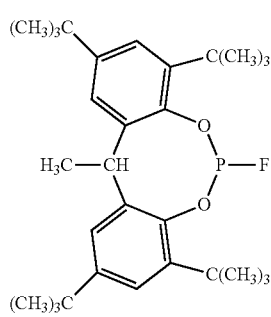
(A)

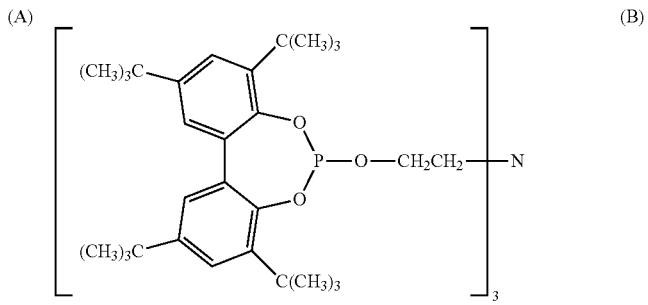
(B)

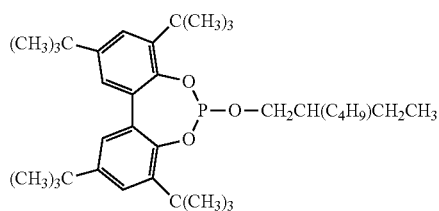
(C)

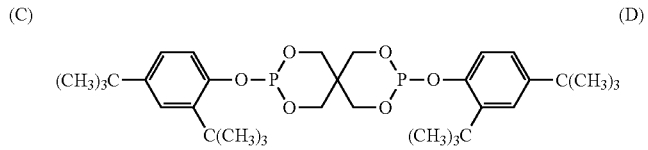
(D)

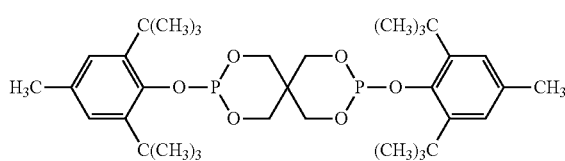
(E)

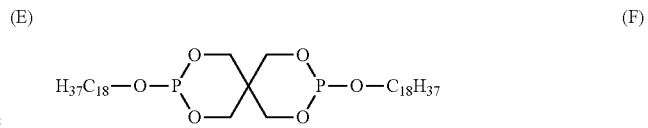
(F)

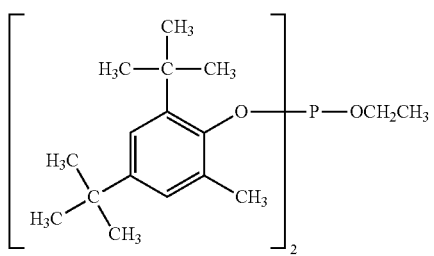
(G)

-continued

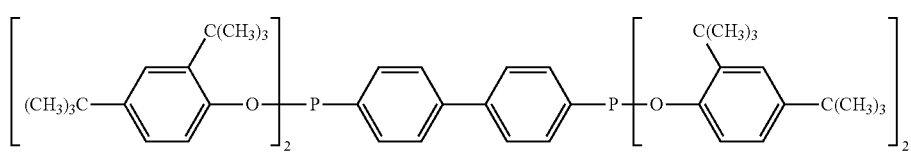
(H)

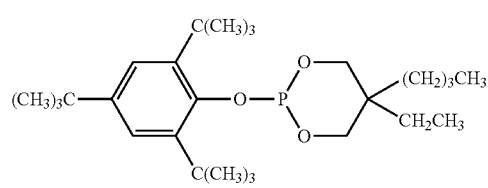
(J)

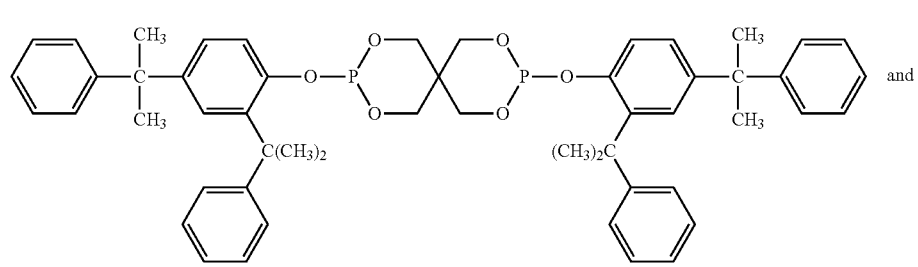
and
(K)

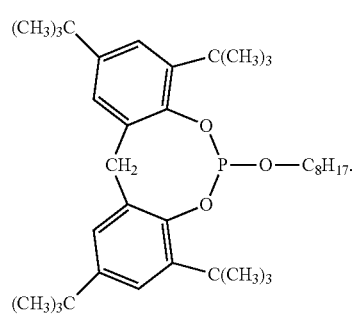
(L)

U.S. Pat. No. 3,096,345 is aimed at acetal and ketal phosphites.

U.S. Pat. No. 6,824,711 teaches tetraphenyl dipropylene glycol diphosphite and tetraphenyl polypropyleneglycol diphosphite, respectively. The target substrate is PVC.

U.S. Pat. No. 3,501,430 discloses tetrakis (nonylphenyl) polypropylene glycol diphosphite. The stabilizers disclosed are for halogen containing resins.

U.S. Pat. No. 3,829,396 is aimed at the stabilization of vinyl chloride resins and diolefin polymers such as butadiene styrene rubber and acrylonitrile butadiene styrene terpolymer. Tetrakis(2,4-di-t-butylphenyl) polypropylene glycol phosphite and tetrakis p-nonylphenyl tripropylene glycol diphosphite are disclosed.

U.S. published app. No. 2007/0254992 is aimed at the stabilization of polymers obtained from a water based latex or emulsion. Disclosed as a stabilizer is tetraphenyl dipropylene glycol diphosphite.

U.S. Pat. No. 7,067,570 is focused on one-part polysiloxane compositions. Phosphite triesters are one component.

JP2005170793 is aimed at organic polyisocyanate compositions. The compositions are stabilized with a combination of a phenol based antioxidant and an organic phosphite compound.

U.S. Pat. No. 4,371,646 is aimed at 2,6-di-tert-butyl phenyl phosphites.

U.S. Pat. No. 4,463,112 teaches organic polyphospites having at least two phosphite ester groups, at least one of which is linked through oxygen to a phenylethylidene-substituted phenyl group and to a residue of a polyhydroxy compound.

U.S. Pat. No. 5,322,871 teaches certain 2,4-di-tert-butyl-6-methyl phosphites.

SUMMARY OF THE INVENTION

It has been found that certain oxyalkylene bridged bis- and tris-phosphite ester mixtures are mobile liquids at ambient conditions. The liquid phosphite mixtures are exceptionally compatible with polyolefins. The liquid phosphite ester mixtures are excellent processing stabilizers.

Disclosed are stabilizer mixtures comprising oxyalkylene bridged bis- and tris-phosphite esters of formulae I and II

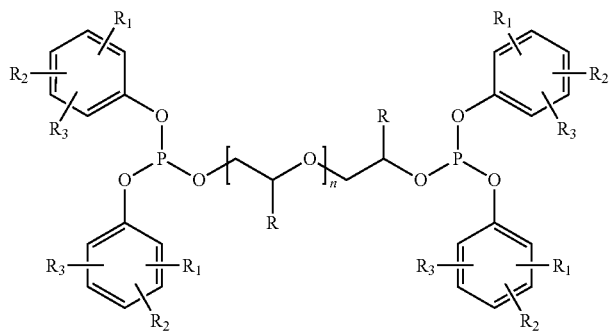

(I)

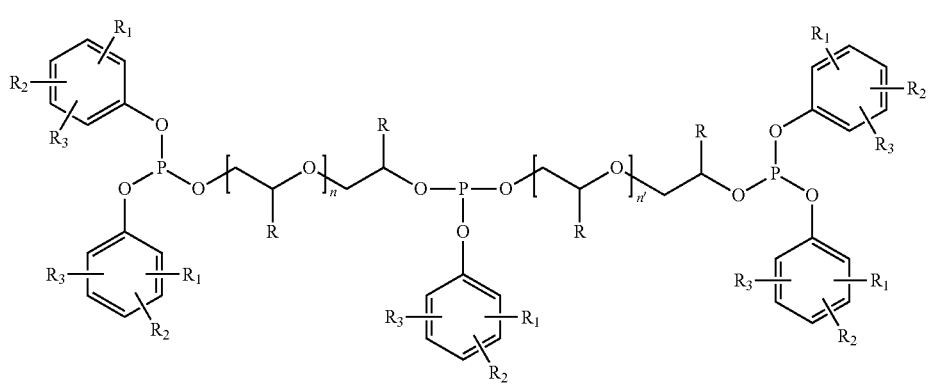

(II)

where
R is hydrogen or methyl,
n and n' are independently an integer from 1 to 45 and
$R_1$, $R_2$ and $R_3$ are each independently hydrogen, straight or branched chain alkyl of 1 to 12 carbon atoms, phenylalkyl of 7 to 9 carbon atoms, phenylalkyl of 7 to 9 carbon atoms substituted on the phenyl ring by one to three straight or branched chain alkyl of 1 to 12 carbon atoms or $R_1$, $R_2$ and $R_3$ are each independently —$(CH_2)_k$—$COOR_4$ where k is 0, 1 or 2 and $R_4$ is hydrogen or straight or branched chain alkyl of 1 to 20 carbon atoms.

Also disclosed are polyolefin compositions stabilized against the deleterious effects of melt processing, heat aging and exposure to combustion products of natural gas, which compositions comprise
a polyolefin substrate and incorporated therein
a stabilizer mixture comprising oxyalkylene bridged bis- and tris-phosphite esters of the formula I and II.

DETAILED DISCLOSURE

The molar ratio of compounds of formula I and II in the mixtures is from about 1:99 to about 99:1. For instance the ratio is from about 1:9 to about 9:1, from about 1:5 to about 5:1, from about 1:3 to about 3:1 or from about 1:2 to about 2:1.

The mixture is prepared by the stepwise reaction of $PCl_3$ with one or more phenol compounds, followed by reaction of the chloridite (phosphorochloridite) intermediate with a polyglycol. The stoichiometry is controlled so as to provide a mixture of compounds of formula I and II. Higher molecular weight analogues are also produced in small amounts, that is the tetra- and penta-phosphite compounds.

The molar stoichiometry of phenol to $PCl_3$ is controlled so as to be below 2:1. For instance, the molar stoichiometry of phenol to $PCl_3$ is from about 1.1 to 1 to about 1.9 to 1. For instance from about 1.3 to 1 to about 1.7 to 1 or from about 1.4 to 1 to about 1.6 to 1.

The polyglycol is polyethylene glycol or polypropylene glycol. The polyglycol is for instance diethylene glycol, dipropylene glycol, triethylene glycol, tripropylene glycol, tetraethylene glycol, tetrapropylene glycol, pentaethylene glycol or pentapropylene glycol. Higher molecular weight polyglycols may also be employed, for example PEG 200 or PEG 300 or higher. A mixture of glycols may be employed.

Thus, n and n' are from 1 to 45, for instance from 2 to 30, from 2 to 10, from 2 to 7 or from 2 to 5.

$R_1$, $R_2$ and $R_3$ are for instance methyl, sec-butyl, tert-butyl, tert-octyl, α-cumyl, nonyl or methyl propanoate.

Alkyl is a branched or unbranched radical, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl or 1,1,3,3,5,5-hexamethylhexyl.

Phenylalkyl is, for example, benzyl, α-methylbenzyl, α,α-dimethylbenzyl or 2-phenylethyl. For example benzyl and α,α-dimethylbenzyl(α-cumyl).

Phenylalkyl substituted on the phenyl radical by 1 or 2 alkyl groups is, for example, 2-methylbenzyl, 3-methylbenzyl, 4-methylbenzyl, 2,4-dimethylbenzyl, 2,6-dimethylbenzyl or 4-tert-butylbenzyl.

The group —$(CH_2)_k COOR_4$ is for instance straight or branched chain $C_1$-$C_{12}$alkyl propanoate, for instance methyl propanoate, —$CH_2CH_2COOMe$.

In the liquid phosphite mixtures the esters of formulae I and II are for instance
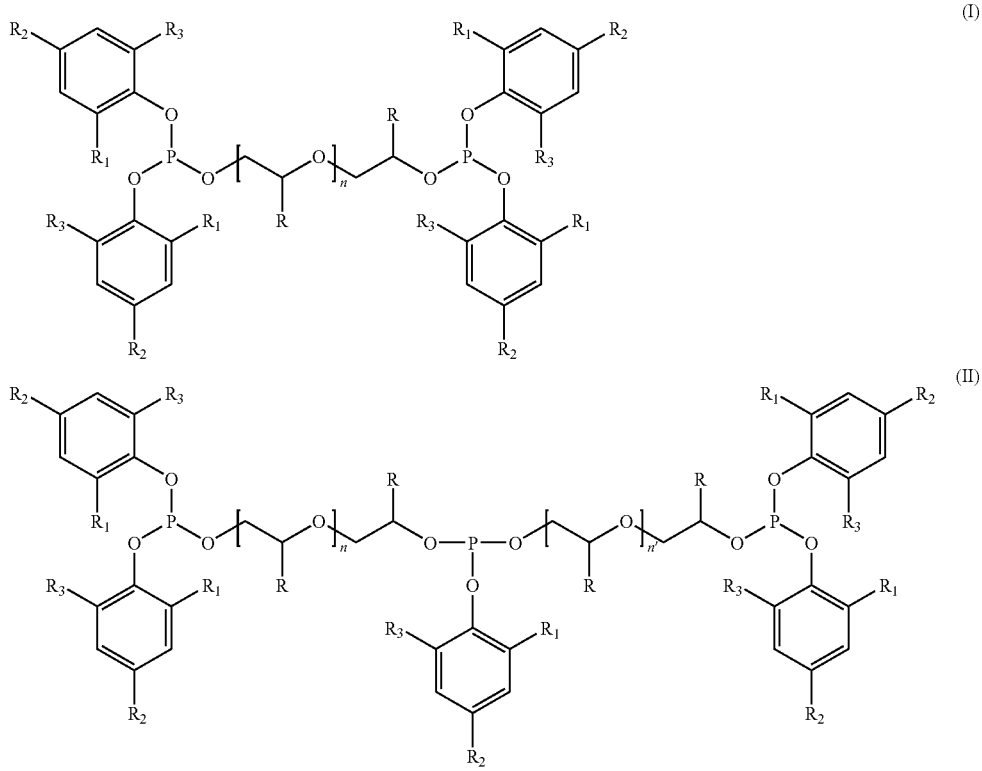
In the liquid phosphite mixtures the esters of formulae I and II are for instance
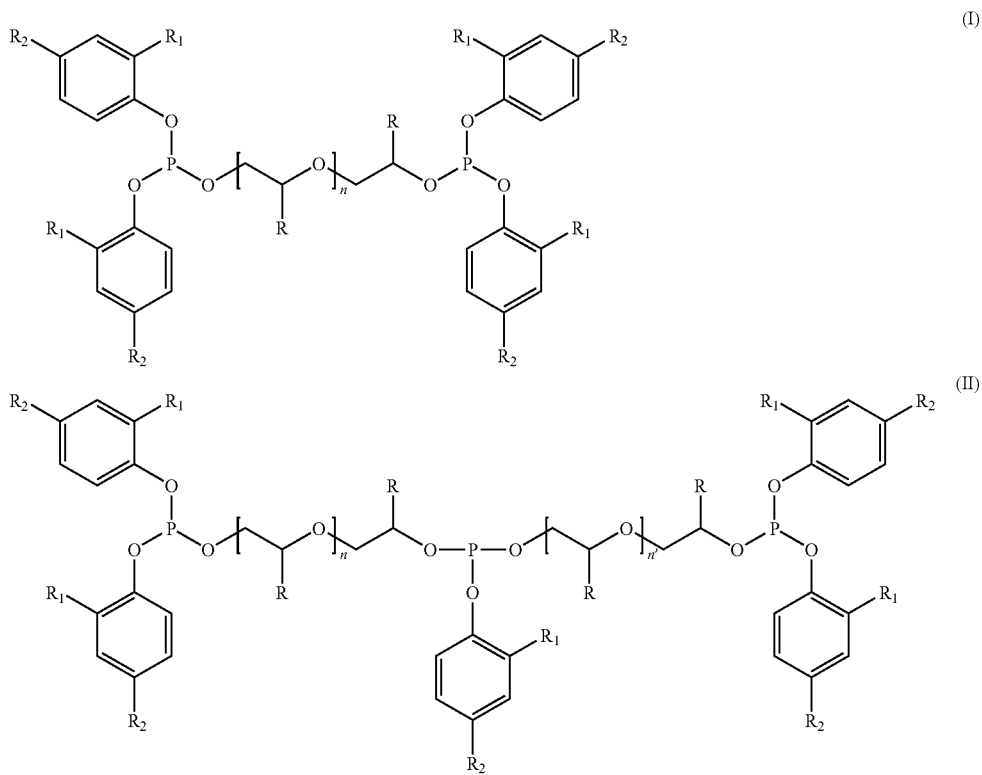

where

R₁ and R₂ are independently methyl, sec-butyl, tert-butyl, tert-octyl, α-cumyl, nonyl or methyl propanoate.

The phosphite mixtures of this invention are necessarily liquid at ambient conditions, 25° C. and 1 atmosphere of pressure. The phosphite mixtures of this invention exhibit an inherent property of being non-migratory from polyolefins (they are inherently non-migratory from polyolefins). The phosphite mixtures are highly compatible with polyolefins.

Examples for polyolefins are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE); both Zeigler-Natta and single site (metallocene, etc.) catalyzed.

Polyolefins, i.e. the polymers of monoolefins exemplified in the preceding paragraph, for example polyethylene and polypropylene, can be prepared by different, and especially by the following, methods:

i) radical polymerization (normally under high pressure and at elevated temperature).

ii) catalytic polymerization using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either p- or s-coordinated. These metal complexes may be in the free form or fixed on substrates, typically on activated magnesium chloride, titanium(III) chloride, alumina or silicon oxide. These catalysts may be soluble or insoluble in the polymerization medium. The catalysts can be used by themselves in the polymerization or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Zeigler (-Natta), TNZ (DuPont), metallocene or single site catalysts (SSC).

2. Mixtures of the polymers mentioned under 1.), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Blends of polymers mentioned under 1.) with impact modifiers such as ethylene-propylene-diene monomer copolymers (EPDM), copolymers of ethylene with higher alpha-olefins (such as ethylene-octene copolymers), polybutadiene, polyisoprene, styrene-butadiene copolymers, hydrogenated styrene-butadiene copolymers, styrene-isoprene copolymers, hydrogenated styrene-isoprene copolymers. These blends are commonly referred to in the industry as TPO's (thermoplastic polyolefins).

Polyolefins of the present invention are for example polypropylene homo- and copolymers and polyethylene homo- and copolymers. For instance, polypropylene, high density polyethylene (HDPE), linear low density polyethylene (LLDPE) and polypropylene random and impact (heterophasic) copolymers. Preferred polyolefins of the present invention include polypropylene homopolymers, polypropylene impact (heterophasic) copolymers, blends thereof, and TPO's such as blends of polypropylene homopolymers and impact copolymers with EPDM or ethylene-alpha-olefin copolymers.

In particular, the present polyolefins are low density polyethylene (LDPE).

Melt processing techniques are know and include for example extrusion, co-kneading, pultrusion, injection molding, co-extrusion, fiber extrusion, fiber spinning, film extrusion (cast, blown, blowmolding), rotational molding, and the like.

The present phosphite mixtures are used for example, in amounts of from about 0.01% to about 5% by weight, based on the weight of the polyolefin, from about 0.025% to about 1%, from about 0.05% to about 0.5% by weight, from about 0.01% to about 1%, about 0.01% to about 0.5%, about 0.025% to about 5%, or about 0.05% to about 5% by weight, based on the weight of the polyolefin to be stabilized. For example, the present phosphites are present at a level of less than about 3% by weight, based on the weight of the polyolefin, or from about 0.01% to about 2.5% by weight, or from about 0.01% to about 2% by weight, based on the weight of the polyolefin.

The incorporation of the present phosphite mixtures and optional further additives into the polyolefin is carried out by known methods, for example before or after molding or also by applying the dissolved or dispersed stabilizer or stabilizer mixture to the polyolefin, with or without subsequent evaporation of the solvent. The stabilizer or stabilizer mixture can also be added to the polyolefins to be stabilized in the form of a masterbatch which contains the present phosphites and optional additives in a concentration of, for example, about 2.5% to about 60% by weight.

The phosphite mixtures and optional further additives can also be added before or during the polymerization or before crosslinking.

The present phosphite mixtures and optional further additives can be incorporated into the polyolefin to be stabilized in pure form or encapsulated in waxes, oils or polymers.

The present phosphite mixtures and optional further additives can also be sprayed onto the polyolefin to be stabilized. They are able to dilute other additives (for example other conventional additives discussed further) or their melts so that they can be sprayed also together with these additives onto the polyolefin to be stabilized. Addition by spraying during the deactivation of the polymerization catalysts is particularly advantageous, it being possible to carry out spraying using, for example, the steam used for deactivation.

In the case of spherically polymerized polyolefins it may, for example, be advantageous to apply the present stabilizers optionally together with other additives, by spraying.

The polyolefin compositions according to the instant invention are useful in the manufacture of polyolefin articles. The said articles are for example woven fibers, non-woven fibers, films, sheets or molded articles.

Further stabilizers include for example hindered phenolic antioxidants, hindered amine light stabilizers, hydroxylamine stabilizers, amine oxide stabilizers, benzofuranone stabilizers and other organic phosphorus stabilizers.

Hindered phenolic antioxidants include for example tris(3, 5-di-tert-butyl-4-hydroxybenzyl)isocyanurate, 1,3,5-tris-(3, 5-di-tert-butyl-4-hydroxybenzyl)-2,4,6-trimethylbenzene, the calcium salt of the monoethyl ester of 3,5-di-tert-butyl-4-hydroxybenzylphosphonic acid, pentaerythritol tetrakis[3-(3,5-di-tert-butyl-4-hydroxyphenyl) propionate] or octadecyl 3-(3,5-di-tert-butyl-4-hydroxyphenyl) propionate.

Hindered amine light stabilizers include for example
the condensate of 1-(2-hydroxyethyl)-2,2,6,6-tetramethyl-4-hydroxypiperidine and succinic acid,

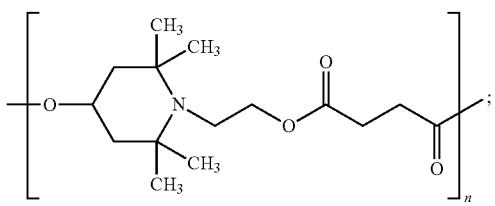

linear or cyclic condensates of N,N'-bis(2,2,6,6-tetramethyl-4-piperidyl)-hexamethylenediamine and 4-tert-octylamino-2,6-dichloro-1,3,5-triazine,

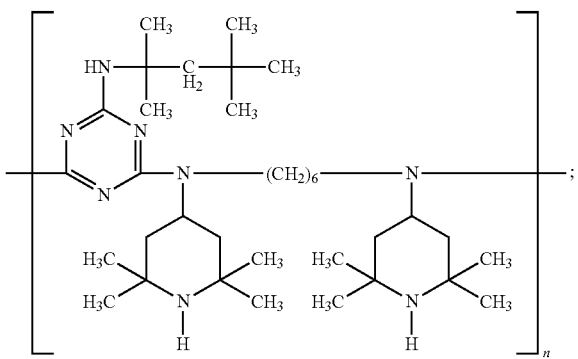

the condensate of 2-chloro-4,6-di-(4-n-butylamino-1,2,2, 6,6-pentamethylpiperidyl)-1,3,5-triazine and 1,2-bis-(3-aminopropylamino)ethane,

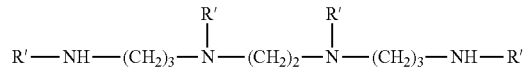

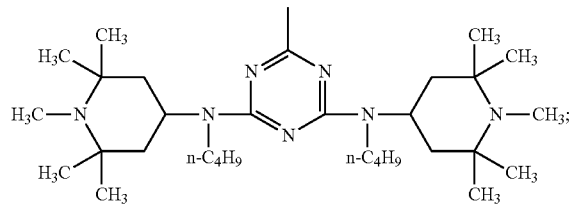

where R' is
the oligomeric compound which is the condensation product of 4,4'-hexamethylene-bis(amino-2,2,6,6-tetramethylpiperidine) and 2,4-dichloro-6-[(2,2,6,6-tetramethylpiperidin-4-yl)butylamino]-s-triazine end-capped with 2-chloro-4,6-bis(dibutylamino)-s-triazine,

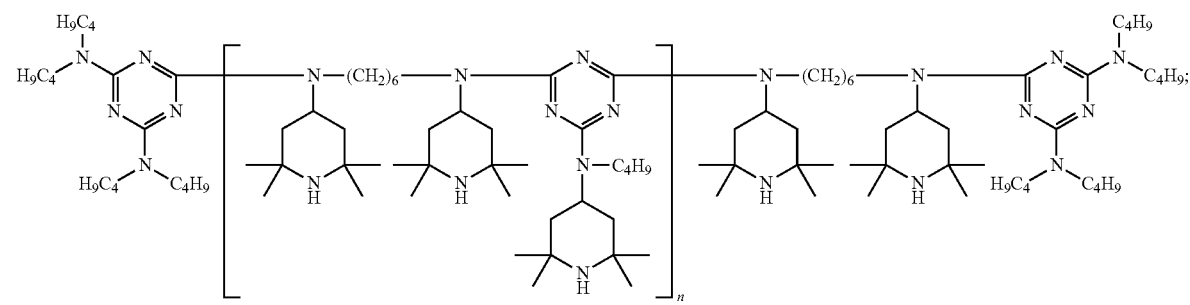

product obtained by reacting a product, obtained by reacting 1,2-bis(3-amino-propylamino)ethane with cyanuric chloride, with (2,2,6,6-tetramethylpiperidin-4-yl)butylamine,

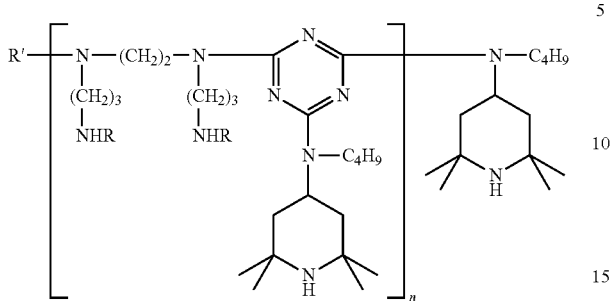

where R'=R or H
and where R=

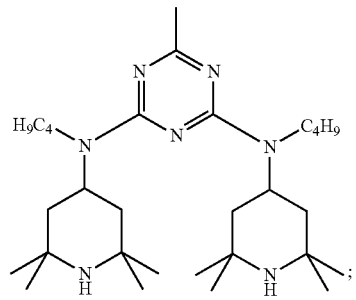

linear or cyclic condensates of N,N'-bis-(2,2,6,6-tetramethyl-4-piperidyl)-hexamethylenediamine and 4-morpholino-2,6-dichloro-1,3,5-triazine,

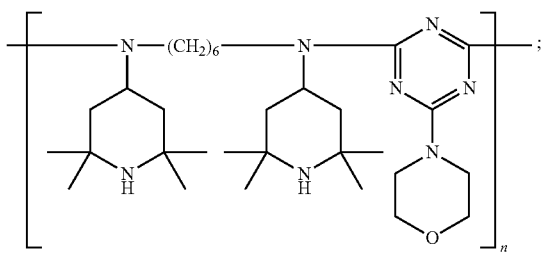

linear or cyclic condensates of N,N'-bis-(1,2,2,6,6-pentamethyl-4-piperidyl)-hexamethylenediamine and 4-morpholino-2,6-dichloro-1,3,5-triazine,

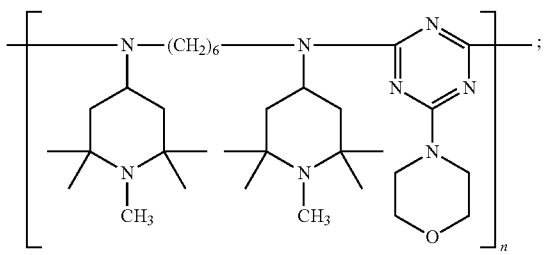

a reaction product of 7,7,9,9-tetramethyl-2-cycloundecyl-1-oxa-3,8-diaza-4-oxospiro[4,5]decane and epichlorohydrin,

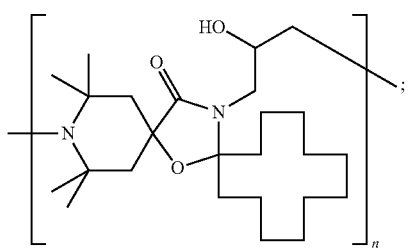

reaction product of maleic acid anhydride-$C_{18}$-$C_{22}$-α-olefin-copolymer with 2,2,6,6-tetramethyl-4-aminopiperidine,

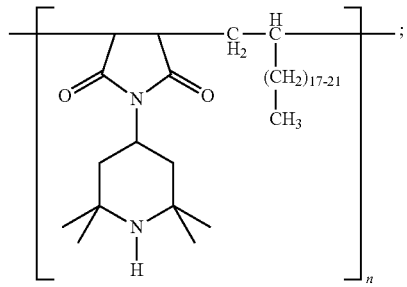

the reaction product of 2,4-bis[(1-cyclohexyloxy-2,2,6,6-piperidin-4-yl)butylamino]-6-chloro-s-triazine with N,N'-bis (3-aminopropyl)ethylenediamine),

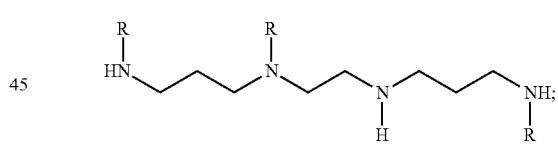

R =

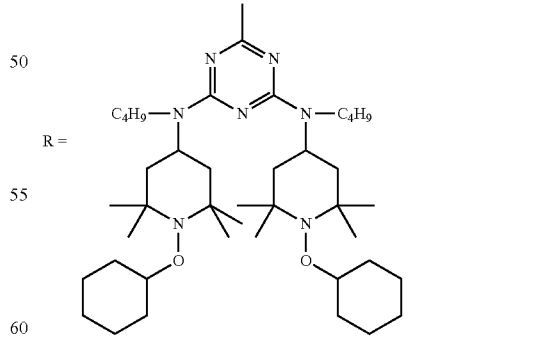

the oligomeric compound which is the condensation product of 4,4'-hexamethylenebis(amino-1-propoxy-2,2,6,6-tetramethylpiperidine) and 2,4-dichloro-6-[(1-propoxy-2,2,6,6-tetramethyl-piperidin-4-yl)butylamino]-s-triazine end-capped with 2-chloro-4,6-bis(dibutylamino)-s-triazine,

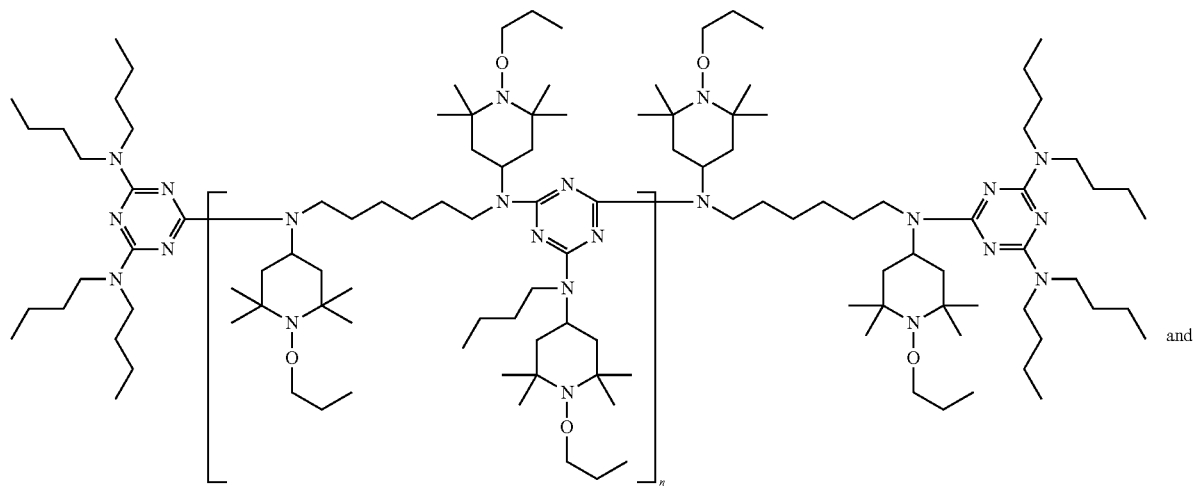

the oligomeric compound which is the condensation product of 4,4'-hexamethylenebis(amino-1,2,2,6,6-pentaamethylpiperidine) and 2,4-dichloro-6-[(1,2,2,6,6-pentaamethylpiperidin-4-yl)butylamino]-s-triazine end-capped with 2-chloro-4,6-bis(dibutylamino)-s-triazine,

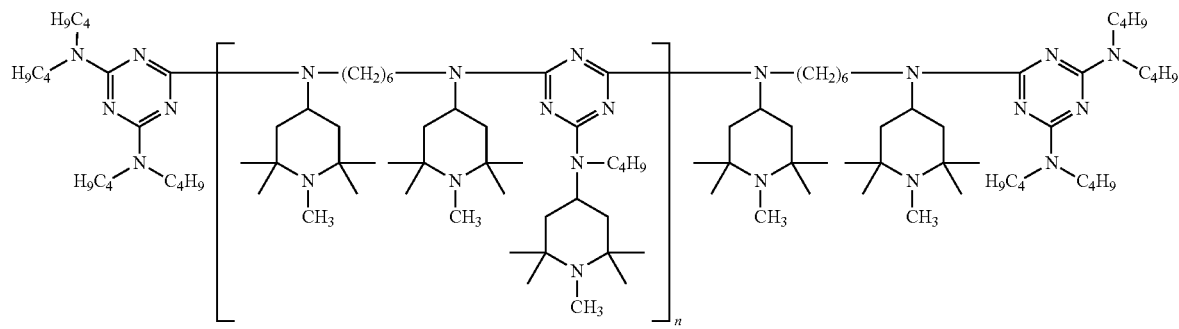

where n is an integer such that the total molecular weight is above about 1000 g/mole.

Hydroxylamine stabilizers are for example N,N-dibenzylhydroxylamine, N,N-diethylhydroxylamine, N,N-dioctylhydroxylamine, N,N-dilaurylhydroxylamine, N,N-didodecylhydroxylamine, N,N-ditetradecylhydroxylamine, N,N-dihexadecylhydroxylamine, N,N-dioctadecylhydroxylamine, N-hexadecyl-N-tetradecylhydroxylamine, N-hexadecyl-N-heptadecylhydroxylamine, N-hexadecyl-N-octadecylhydroxylamine, N-heptadecyl-N-octadecylhydroxylamine, N-methyl-N-octadecylhydroxylamine or N,N-di(hydrogenated tallow)hydroxylamine.

The amine oxide stabilizer is for example GENOX EP, a di($C_{16}$-$C_{18}$)alkyl methyl amine oxide, CAS#204933-93-7.

Benzofuranone stabilizers are for example 3-(4-(2-acetoxyethoxy)phenyl)-5,7-di-tert-butyl-benzofuran-2-one, 5,7-di-tert-butyl-3-(4-(2-stearoyloxyethoxy)phenyl)benzofuran-2-one, 3,3'-bis(5,7-di-tert-butyl-3-(4-(2-hydroxyethoxy)phenyl)benzofuran-2-one), 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one or 3-(2,3-dimethylphenyl)-5,7-di-tert-butyl-benzofuran-2-one.

Further organic phosphorus stabilizers are for example those as disclosed previously. Further organic phosphorus stabilizers are also for example those as disclosed in U.S. Pat. No. 6,541,549 and U.S. Pat. app. No. 2003/0096890, the disclosures of which are hereby incorporated by reference.

These optional stabilizers are employed at the same levels as the present phosphite mixtures.

In addition to the present phosphite mixtures and the above optional stabilizers, the following further additives may also be employed. These further stabilizers are employed for example at use levels from about 0.01% to about 5% by weight, based on the weight of the polyolefin.

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1-methylundec-1-yl)phenol, 2,4-dimethyl-6-(1-methylheptadec-1-yl)phenol, 2,4-dimethyl-6-(1-methyltridec-1-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2, 2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl) disulfide.

1.6. Alkylidenebisphenols, for example 2, 2'-methylenebis(6-tert-butyl-4-methylphenol), 2,2'-methylenebis(6-tert-butyl-4-ethylphenol), 2,2'-methylenebis[4-methyl-6-α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-α-methylbenzyl)-4-nonylphenol], 2,2'-methylenebis[6-(α,α-dimethylbenzyl)-4-nonylphenol], 4,4'-methylenebis(2, 6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3-tert-butyl-4-hydroxyphenyl) butyrate], bis(3-tert-butyl-4-hydroxy-5-methyl-phenyl)dicyclopentadiene, bis[2-(3' tert-butyl-2-hydroxy-5-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1, 5,5-tetra-(5-tert-butyl-4-hydroxy-2-methylphenyl)pentane.

1.7. Benzyl compounds, for example 3, 5,3',5'-tetra-tert-butyl-4,4'-dihydroxydibenzyl ether, octadecyl-4-hydroxy-3, 5-dimethylbenzylmercaptoacetate, tridecyl-4-hydroxy-3,5-di-tert-butylbenzylmercaptoacetate, tris(3,5-di-tert-butyl-4-hydroxybenzyl)amine, 1,3,5-tri-(3,5-di-tert-butyl-4-hydroxybenzyl)-2,4,6-trimethylbenzene, di-(3,5-di-tert-butyl-4-hydroxybenzyl) sulfide, 3,5-di-tert-butyl-4-hydroxybenzyl-mercapto-acetic acid isooctyl ester, bis-(4-tert-butyl-3-hydroxy-2,6-dimethylbenzyl)dithiol terephthalate, 1,3,5-tris-(3,5-di-tert-butyl-4-hydroxybenzyl) isocyanurate, 1,3,5-tris-(4-tert-butyl-3-hydroxy-2,6-dimethylbenzyl) isocyanurate, 3,5-di-tert-butyl-4-hydroxybenzyl-phosphoric acid dioctadecyl ester and 3,5-di-tert-butyl-4-hydroxybenzyl-phosphoric acid monoethyl ester, calcium-salt.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl) malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2, 3,5,6-tetramethylbenzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris-(3,5-di-tert-butyl-4-hydroxyphenoxy)-1,2,3-triazine, 1,3,5-tris-(3,5-di-tert-butyl-4-hydroxy-benzyl)isocyanurate, 1,3,5-tris(4-tert-butyl-3-hydroxy-2,6-dimethylbenzyl)isocyanurate, 2,4, 6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxy-lauric acid anilide, 4-hydroxystearic acid anilide, 2,4-bis-octylmercapto-6-(3,5-tert-butyl-4-hydroxyanilino)-s-triazine and octyl-N-(3,5-di-tert-butyl-4-hydroxyphenyl)-carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane.

1.14. Esters of β-(5-tert-butyl-4-hydroxy-3-methylphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane.

1.15. Esters of β-(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis (hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis (hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl)trimethylenediamide, N,N'-bis(3,5-di-tert-butyl-4-hydroxyphenylpropionyphydrazide, N,N'-bis[2-(3-[3,5-di-tert-butyl-4-hydroxyphenyl] propionyloxy)ethyl]oxamide (Naugard®XL-1 supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyl-diphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octylphenothiazines, N-allylphenothiazin, N,N,N',N'-tetraphenyl-1,4-diaminobut-2-ene, N,N-bis-(2,2,6,6-tetramethyl-piperid-4-yl-hexamethylenediamine, bis(2,2,6,6-tetramethylpiperid-4-yl)-sebacate, 2,2,6,6-tetramethylpiperidin-4-one, 2,2,6,6-tetramethylpiperidin-4-ol.

2. UV Absorbers and Light Stabilizers 2.1. 2-(2-Hydroxyphenyl)-2H-benzotriazoles, for example known commercial hydroxyphenyl-2H-benzotriazoles and benzotriazoles as disclosed in, U.S. Pat. Nos. 3,004,896; 3,055,896; 3,072,585; 3,074,910; 3,189,615; 3,218,332; 3,230,194; 4,127,586; 4,226,763; 4,275,004; 4,278,589; 4,315,848; 4,347,180; 4,383,863; 4,675,352; 4,681,905, 4,853,471; 5,268,450; 5,278,314; 5,280,124; 5,319,091; 5,410,071; 5,436,349; 5,516,914; 5,554,760; 5,563,242; 5,574,166; 5,607,987, 5,977,219 and 6,166,218 such as 2-(2-hydroxy-5-methylphenyl)-2H-benzotriazole, 2-(3,5-di-t-butyl-2-hydroxyphenyl)-2H-benzotriazole, 2-(2-hydroxy-5-t-butylphenyl)-2H-benzotriazole, 2-(2-hydroxy-5-t-octylphenyl)-2H-benzotriazole, 5-chloro-2-(3,5-di-t-butyl-2-hydroxyphenyl)-2H-benzotriazole, 5-chloro-2-(3-t-butyl-2-hydroxy-5-methylphenyl)-2H-benzotriazole, 2-(3-sec-butyl-5-t-butyl-2-hydroxyphenyl)-2H-benzotriazole, 2-(2-hydroxy-4-octyloxyphenyl)-2H-benzotriazole, 2-(3,5-di-t-amyl-2-hydroxyphenyl)-2H-benzotriazole, 2-(3,5-bis-α-cumyl-2-hydroxyphenyl)-2H-benzotriazole, 2-(3-t-butyl-2-hydroxy-5-(2-(ω-hydroxy-octa-(ethyleneoxy)carbonyl-ethyl)-, phenyl)-2H-benzotriazole, 2-(3-dodecyl-2-hydroxy-5-methylphenyl)-2H-benzotriazole, 2-(3-t-butyl-2-hydroxy-5-(2-octyloxycarbonyl)ethylphenyl)-2H-benzotriazole, dodecylated 2-(2-hydroxy-5-methylphenyl)-2H-benzotriazole, 2-(3-t-butyl-2-hydroxy-5-(2-octyloxycarbonylethyl)phenyl)-5-chloro-2H-benzotriazole, 2-(3-tert-butyl-5-(2-(2-ethylhexyloxy)-carbonylethyl)-2-hydroxyphenyl)-5-chloro-2H-benzotriazole, 2-(3-t-butyl-2-hydroxy-5-(2-methoxycarbonylethyl)phenyl)-5-chloro-2H-benzotriazole, 2-(3-t-butyl-2-hydroxy-5-(2-methoxycarbonylethyl)phenyl)-2H-benzotriazole, 2-(3-t-butyl-5-(2-(2-ethylhexyloxy)carbonylethyl)-2-hydroxyphenyl)-2H-benzotriazole, 2-(3-t-butyl-2-hydroxy-5-(2-isooctyloxycarbonylethyl)phenyl-2H-benzotriazole, 2,2'-methylene-bis(4-t-octyl-(6-2H-benzotriazol-2-yl)phenol), 2-(2-hydroxy-3-α-cumyl-5-t-octylphenyl)-2H-benzotriazole, 2-(2-hydroxy-3-t-octyl-5-α-cumylphenyl)-2H-benzotriazole, 2-(2-hydroxy-3,5-di-α-cumyl-phenyl)-2H-benzotriazole, 5-chloro-2-(2-hydroxy-3,5-di-α-cumylphenyl)-2H-benzotriazole, 5-chloro-2-(2-hydroxy-3-α-cumyl-5-t-octylphenyl)-2H-benzotriazole, 2-(3-t-butyl-2-hydroxy-5-(2-isooctyloxycarbonylethyl)phenyl)-5-chloro-2H-benzotriazole, 5-trifluoromethyl-2-(2-hydroxy-3-α-cumyl-5-t-octylphenyl)-2H-benzotriazole, 5-trifluoromethyl-2-(2-hydroxy-5-t-octylphenyl)-2H-benzotriazole, 5-trifluoromethyl-2-(2-hydroxy-3,5-di-t-octylphenyl)-2H-benzotriazole, methyl 3-(5-trifluoromethyl-2H-benzotriazol-2-yl)-5-t-butyl-4-hydroxyhydrocinnamate, 5-butylsulfonyl-2-(2-hydroxy-3-α-cumyl-5-t-octylphenyl)-2H-benzotriazole, 5-trifluoromethyl-2-(2-hydroxy-3-α-cumyl-5-t-butylphenyl)-2H-benzotriazole, 5-trifluoromethyl-2-(2-hydroxy-3,5-di-t-butylphenyl)-2H-benzotriazole, 5-trifluoromethyl-2-(2-hydroxy-3,5-di-α-cumylphenyl)-2H-benzotriazole, 5-butylsulfonyl-2-(2-hydroxy-3,5-di-t-butylphenyl)-2H-benzotriazole and 5-phenylsulfonyl-2-(2-hydroxy-3,5-di-t-butylphenyl)-2H-benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tert-butylphenyl salicylate, phenyl salicylate, octylphenyl salicylate, dibenzoyl resorcinol, bis(4-tert-butylbenzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates and malonates, for example, α-cyano-β,β-diphenylacrylic acid ethyl ester or isooctyl ester, α-carbomethoxy-cinnamic acid methyl ester, α-cyano-β-methyl-p-methoxycinnamic acid methyl ester or butyl ester, α-carbomethoxy-p-methoxy-cinnamic acid methyl ester, N-(β-carbomethoxy-β-cyanoyinyl)-2-methyl-indoline, Sanduvor® PR25, dimethyl p-methoxybenzylidenemalonate (CAS#7443-25-6), and Sanduvor® PR31, di-(1,2,2,6,6-pentamethylpiperidin-4-yl) p-methoxybenzylidenemalonate (CAS #147783-69-5).

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amine stabilizers, for example 4-hydroxy-2,2,6,6-tetramethylpiperidine, 1-allyl-4-hydroxy-2,2,6,6-tetramethylpiperidine, 1-benzyl-4-hydroxy-2,2,6,6-tetramethylpiperidine, bis(2,2,6,6-tetramethyl-4-piperidyl) sebacate, bis(2,2,6,6-tetramethyl-4-piperidyl) succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6, 6-tetramethyl-4-piperidyl)hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6, 6-tetramethylpiperidine, bis(1,2,2,6,6-pentamethylpiperidyl)-2-n-butyl-2-(2-hydroxy-3,5-di-tert-butylbenzyl) malonate, 3-n-octyl-7,7,9,9-tetramethyl-1,3,8-triazaspiro [4.5]decan-2,4-dione, bis(1-octyloxy-2,2,6,6-tetramethylpiperidyl) sebacate, bis(1-octyloxy-2,2,6,6-tetramethylpiperidyl) succinate, linear or cyclic condensates of N,N'-bis-(2, 2,6,6-tetramethyl-4-piperidyl)-hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-amino-propylamino) ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9- tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl) pyrrolidine-2,5-dione, a mixture of 4-hexadecyloxy- and 4-stearyloxy-2,2,6,6-tetramethylpiperidine, a condensation product of N,N'-bis(2,2,6,6-tetramethyl-4-piperidyl)hexamethylenediamine and 4-cyclohexylamino-2,6-dichloro-1,3,5-triazine, a condensation product of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9-tetramethyl-1-oxa-3,8-diaza-4-oxo-spiro[4,5]decane, a reaction product of 7,7,9,9-tetramethyl-2-cycloundecyl-1-oxa-3,8-diaza-4-oxospiro [4,5]decane and epichlorohydrin, 1,1-bis(1,2,2,6,6-pentamethyl-4-piperidyloxycarbonyl)-2-(4-methoxyphenyl) ethene, N,N'-bis-formyl-N,N'-bis(2,2,6,6-tetramethyl-4-piperidyl)hexamethylenediamine, diester of 4-methoxymethylene-malonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic acid anhydride-α-olefin-copolymer with 2,2,6,6-tetramethyl-4-aminopiperidine or 1,2,2,6,6-pentamethyl-4-aminopiperidine.

The sterically hindered amine may also be one of the compounds described in U.S. Pat. No. 5,980,783, the relevant parts of which are hereby incorporated by reference, that is compounds of component I-a), I-b), I-c), I-d), I-e), I-f), I-g), I-h), I-i), I-j), I-k) or I-l), in particular the light stabilizer 1-a-1, 1-a-2, 1-b-1, 1-c-1, 1-c-2, 1-d-1, 1-d-2, 1-d-3, 1-e-1, 1-f-1, 1-g-1, 1-g-2 or 1-k-1 listed on columns 64-72 of said U.S. Pat. No. 5,980,783.

The sterically hindered amine may also be one of the compounds described in U.S. Pat. Nos. 6,046,304 and 6,297,299, the disclosures of which are hereby incorporated by reference, for example compounds as described in claim 10 or 38 or in Examples 1-12 or D-1 to D-5 therein.

2.7. Sterically hindered amines substituted on the N-atom by a hydroxy-substituted alkoxy group, for example compounds such as 1-(2-hydroxy-2-methylpropoxy)-4-octadecanoyloxy-2,2,6,6-tetramethylpiperidine, 1-(2-hydroxy-2-methylpropoxy)-4-hexadecanoyloxy-2,2,6,6-tetramethylpiperidine, the reaction product of 1-oxyl-4-hydroxy-2,2,6,6-tetramethylpiperidine with a carbon radical from t-amylalcohol, 1-(2-hydroxy-2-methylpropoxy)-4-hydroxy-2,2,6,6-tetramethylpiperidine, 1-(2-hydroxy-2-methylpropoxy)-4-oxo-2,2,6,6-tetramethylpiperidine, bis(1-(2-hydroxy-2-methylpropoxy)-2,2,6,6-tetramethylpiperidin-4-yl) sebacate, bis(1-(2-hydroxy-2-methylpropoxy)-2,2,6,6-tetramethylpiperidin-4-yl) adipate, bis(1-(2-hydroxy-2-methylpropoxy)-2,2,6,6-tetramethylpiperidin-4-yl) succinate, bis(1-(2-hydroxy-2-methylpropoxy)-2,2,6,6-tetramethylpiperidin-4-yl) glutarate and 2,4-bis{N-[1-(2-hydroxy-2-methylpropoxy)-2,2,6,6-tetramethylpiperidin-4-yl]-N-butylamino}-6-(2-hydroxyethyl-amino)-s-triazine.

2.8. Oxamides, for example 4, 4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.9. Tris-aryl-o-hydroxyphenyl-s-triazines, for example known commercial tris-aryl-o-hydroxyphenyl-s-triazines and triazines as disclosed in, U.S. Pat. Nos. 3,843,371; 4,619,956; 4,740,542; 5,096,489; 5,106,891; 5,298,067; 5,300,414; 5,354,794; 5,461,151; 5,476,937; 5,489,503; 5,543,518; 5,556,973; 5,597,854; 5,681,955; 5,726,309; 5,736,597; 5,942,626; 5,959,008; 5,998,116; 6,013,704; 6,060,543; 6,187,919; 6,242,598 and 6,468,958, for example 4,6-bis-(2,4-dimethylphenyl)-2-(2-hydroxy-4-octyloxyphenyl)-s-triazine, Cyasorb® 1164, Cytec Corp, 4,6-bis-(2,4-dimethylphenyl)-2-(2,4-dihydroxyphenyl)-s-triazine, 2,4-bis(2,4-dihydroxyphenyl)-6-(4-chlorophenyl)-s-triazine, 2,4-bis[2-hydroxy-4-(2-hydroxy-ethoxy)phenyl]-6-(4-chlorophenyl)-s-triazine, 2,4-bis[2-hydroxy-4-(2-hydroxy-4-(2-hydroxyethoxy)phenyl]-6-(2,4-dimethylphenyl)-s-triazine, 2,4-bis[2-hydroxy-4-(2-hydroxyethoxy)phenyl]-6-(4-bromophenyl)-s-triazine, 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine, 2,4-bis(4-biphenylyl)-6-(2-hydroxy-4-octyloxycarbonylethylideneoxyphenyl)-s-triazine, 2-phenyl-4-[2-hydroxy-4-(3-sec-butyloxy-2-hydroxypropyloxy)phenyl]-6-[2-hydroxy-4-(3-sec-amyloxy-2-hydroxypropyloxy)-phenyl]-s-triazine, 2,4-bis(2,4-dimethylphenyl)-6-[2-hydroxy-4-(3-benzyloxy-2-hydroxy-propyloxy) phenyl]-s-triazine, 2,4-bis(2-hydroxy-4-n-butyloxyphenyl)-6-(2,4-di-n-butyloxyphenyl)-s-triazine, 2,4-bis(2,4-dimethylphenyl)-6-[2-hydroxy-4-(3-nonyloxy*-2-hydroxypropyloxy)-5-α-cumylphenyl]-s-triazine (* denotes a mixture of octyloxy, nonyloxy and decyloxy groups), methylenebis-{2,4-bis(2,4-dimethylphenyl)-6-[2-hydroxy-4-(3-butyloxy-2-hydroxypropoxy)-phenyl]-s-triazine}, methylene bridged dimer mixture bridged in the 3:5', 5:5' and 3:3' positions in a 5:4:1 ratio, 2,4,6-tris(2-hydroxy-4-isooctyloxycarbonylisopropylideneoxyphenyl)-s-triazine, 2,4-bis(2,4-dimethylphenyl)-6-(2-hydroxy-4-hexyloxy-5-α-cumylphenyl)-s-triazine, 2-(2,4,6-trimethyl-phenyl)-4,6-bis[2-hydroxy-4-(3-butyloxy-2-hydroxypropyloxy)phenyl]-s-triazine, 2,4,6-tris[2-hydroxy-4-(3-sec-butyloxy-2-hydroxypropyloxy)phenyl]-s-triazine, mixture of 4,6-bis-(2,4-dimethylphenyl)-2-(2-hydroxy-4-(3-dodecyloxy-2-hydroxypropoxy)-phenyl)-s-triazine and 4,6-bis-(2,4-dimethylphenyl)-2-(2-hydroxy-4-(3-tridecyloxy-2-hydroxypropoxy)-phenyl)-s-triazine, 4,6-bis-(2,4-dimethylphenyl)-2-(2-hydroxy-4-(3-(2-ethylhexyloxy)-2-hydroxypropoxy)-phenyl)-s-triazine and 4,6-diphenyl-2-(4-hexyloxy-2-hydroxyphenyl)-s-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris (2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl) pentaerythritol diphosphite, bis(2,4,6-tris(tert-butylphenyl) pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-dibenzo[d,f] [1,3,2]dioxaphosphepin, 6-fluoro-2,4,8,10-tetra-tert-butyl-12-methyl-dibenzo[d,g][1,3,2]dioxaphosphocin, bis(2,4-di-tert-butyl-6-methylphenyl)methyl phosphite, bis(2,4-di-tert-butyl-6-methylphenyl)ethyl phosphite, 2,2',2"-nitrilo [triethyltris(3,3',5,5'-tetra-tert-butyl-1,1'-biphenyl-2,2'-diyl) phosphite], 2-ethylhexyl(3,3',5,5'-tetra-tert-butyl-1,1'-biphenyl-2,2'-diyl)phosphite.

Especially preferred are the following phosphites:

Tris(2,4-di-tert-butylphenyl) phosphite, tris(nonylphenyl) phosphite

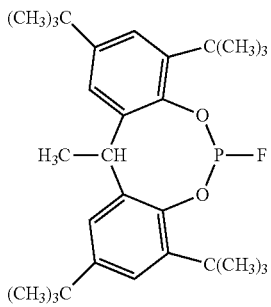

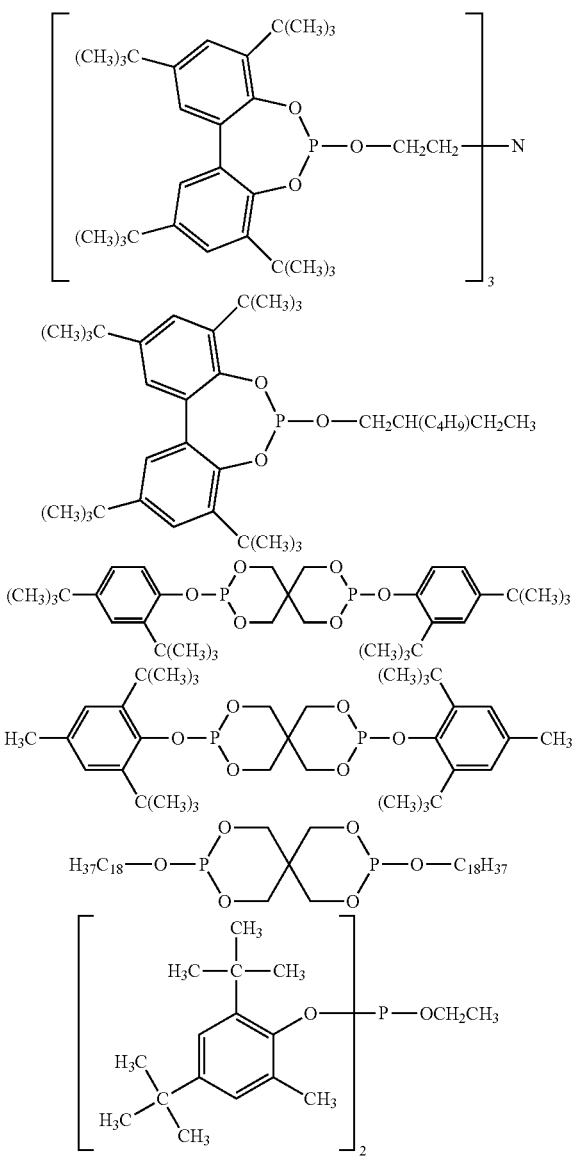

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N-methyl-N-octadecylhydroxylamine and the N,N-dialkylhydroxylamine derived from hydrogenated tallow amine.

6. Nitrones, for example N-benzyl-α-phenylnitrone, N-ethyl-α-methylnitrone, N-octyl-α-heptylnitrone, N-lauryl-α-undecylnitrone, N-tetradecyl-α-tridcylnitrone, N-hexadecyl-α-pentadecylnitrone, N-octadecyl-α-heptadecylnitrone, N-hexadecyl-α-heptadecylnitrone, N-ocatadecyl-α-pentadecylnitrone, N-heptadecyl-α-heptadecylnitrone, N-octadecyl-α-hexadecylnitrone, N-methyl-α-heptadecylnitrone and the nitrone derived from N,N-dialkylhydroxylamine derived from hydrogenated tallow amine.

7. Amine oxides, for example amine oxide derivatives as disclosed in U.S. Pat. Nos. 5,844,029 and 5,880,191, didecyl methyl amine oxide, tridecyl amine oxide, tridodecyl amine oxide and trihexadecyl amine oxide.

8. Benzofuranones and indolinones, for example those disclosed in U.S. Pat. No. 4,325,863, 4,338,244, 5,175,312, 5,216,052, 5,252,643 5,369,159 5,356,966 5,367,008 5,428,177 or 5,428,162 or 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one, Irganox® HP-136, Ciba Specialty Chemicals Corp., and 3-(2,3-dimethylphenyl)-5,7-di-tert-butyl-benzofuran-2-one.

9. Thiosynergists, for example dilauryl thiodipropionate or distearyl thiodipropionate.

10. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

11. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example, calcium stearate, zinc stearate, magnesium behenate, magnesium stearate, sodium ricinoleate and potassium palmitate, antimony pyrocatecholate or zinc pyrocatecholate.

12. Nucleating agents, for example inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers).

13. Fillers and reinforcing agents, for example calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

14. Dispersing Agents, such as polyethylene oxide waxes or mineral oil.

15. Other additives, for example plasticizers, lubricants, emulsifiers, pigments, dyes, optical brighteners, rheology additives, catalysts, flow-control agents, slip agents, crosslinking agents, crosslinking boosters, halogen scavengers, smoke inhibitors, flameproofing agents, antistatic agents, clarifiers such as substituted and unsubstituted bis-benzylidene sorbitols, benzoxazinone UV absorbers such as 2,2'-p-phenylene-bis(3,1-benzoxazin-4-one), Cyasorb® 3638 (CAS#18600-59-4), and blowing agents.

The fillers and reinforcing agents (item 13 in the list), for example talc, calcium carbonate, mica or kaolin, are added to the polyolefins in concentrations of about 0.01% to about 40% by weight, based on the overall weight of the polyolefins to be stabilized.

The fillers and reinforcing agents (item 13 in the list), for example metal hydroxides, especially aluminum hydroxide or magnesium hydroxide, are added to the polyolefins in concentrations of about 0.01% to about 60% by weight, based on the overall weight of the polyolefins to be stabilized.

Carbon black as filler is added to the polyolefins in concentrations, judiciously, of from about 0.01% to about 5% by weight, based on the overall weight of the polyolefins to be stabilized.

Glass fibers as reinforcing agents are added to the polyolefins in concentrations, judiciously, of from about 0.01% to about 20% by weight, based on the overall weight of the polyolefins to be stabilized.

EXAMPLES

The following Examples illustrate the invention in more detail. Unless indicated otherwise, all parts and percentages are by weight. For synthetic Examples, all apparatus are flamed dried under dried nitrogen before use.

Synthetic Examples

Example 1

Triethylene glycol bis[di(2,4-di-tert-butylphenyl)]phosphite

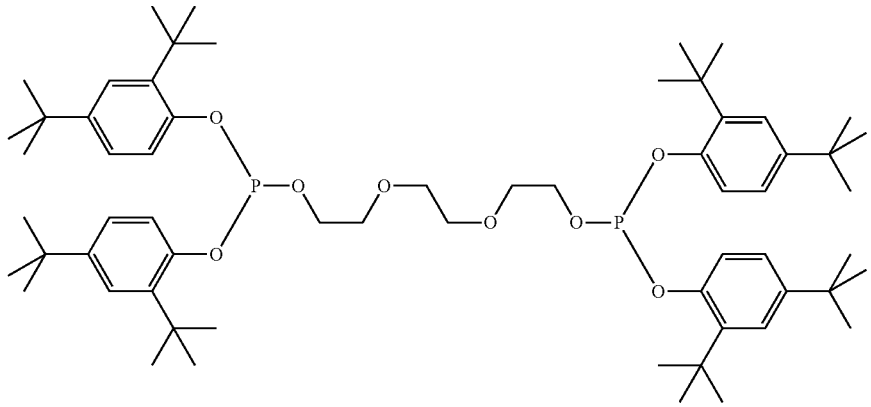

Into a solution of 3.2 g (21.5 mmol) of triethylene glycol and 13.1 g (130 mmol) of triethylamine in 200 mL of toluene is added dropwise a solution of 20.4 g (43 mmol) of bis(2,4-di-tert-butylphenoxy)chlorophosphine in 100 mL of toluene. After addition is complete in 20 minutes, the reaction mixture is a yellowish suspension. After two hours of stirring at ambient temperature, the reaction mixture is filtered through a pack of basic alumina and rinsed twice with 300 mL of toluene. All filtrates are combined and concentrated to a total of 18 g of thick oil in 81% yield.

Example 2

Tripropylene glycol bis[di(2,4-di-tert-butylphenyl)]phosphite

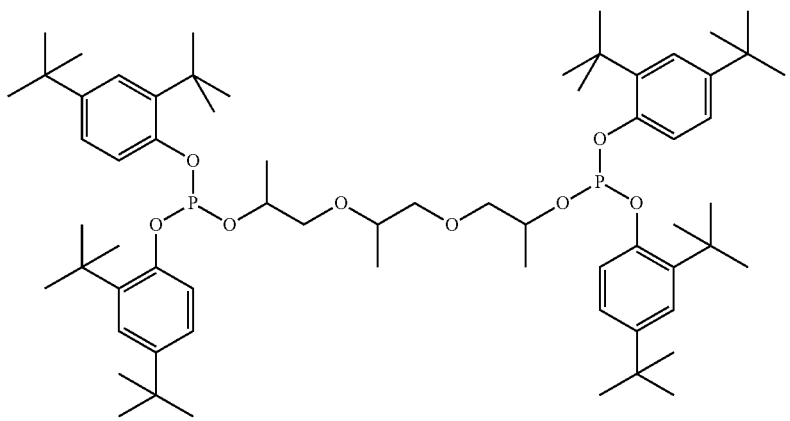

Into a solution of 2.42 g (7.5 mmol) of tetrabutylammonium bromide and 154.8 g (750 mmol) of 2,4-di-tert-butylphenol in 150 g of heptane is added dropwise 52.6 g (375 mmol) of phosphorus trichloride over 1 hour. The solution is held at 60°-65° C. for 3 hours and sparged with nitrogen. Into the resulting phosphorochloridite solution is then added 75 g (765 mmol) of triethylamine followed by filtration to remove the triethylamine hydrochloride salt. Into the filtrate is added dropwise 36.1 g (187.5 mmol) of tripropylene glycol while maintaining the reaction temperature below 60° C. After the addition, the reaction mixture is allowed to stir for an additional 2 hours. The reaction mass is filtered and the filtrate is concentrated in vacuo at 70°-75° C. to give a yellow, viscous oil.

Example 3

PEG 200 bis[di(2,4-di-tert-butylphenyl)]phosphite

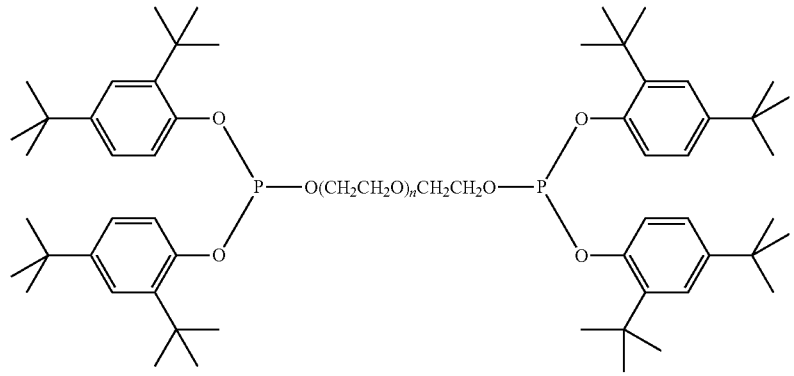

The procedure of Example 2 is repeated using 52.5 g (375 mmol) of phosphorus trichloride, 2.41 g (7.5 mmol) of tetrabutylammonium bromide, 154.6 g (750 mmol) of 2,4-di-tert-butylphenol, 75 g (765 mmol) of triethylamine, 36.75 g (187.5 mmol) of PEG 200 and a total of 150 g heptane to give a yellow, viscous syrup.

Example 4

PEG 200 Bis{di[2-t-butyl-4-(methoxycarboxyprop-3-yl)phenyl]}phosphite

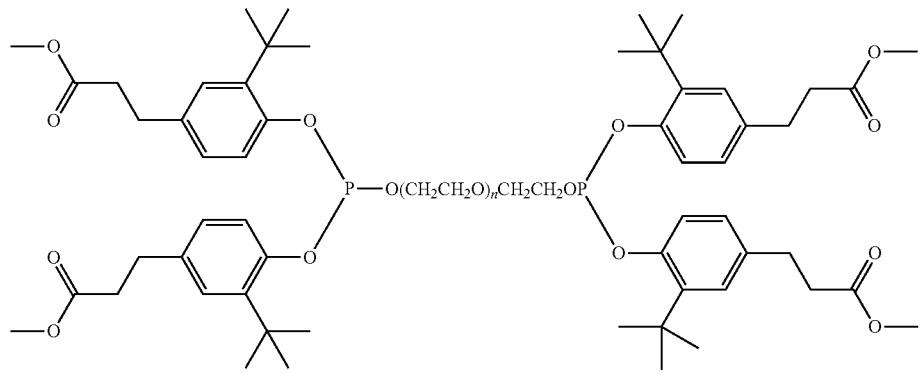

A. Into a mixture of 17.7 g (130 mmol) of phosphorus trichloride, 62 g (250 mmol) of methyl 3-tert-butyl-4-hydroxyhydrocinnamate in 150 g of toluene is added dropwise a solution of 37.3 g (250 mmol) of N,N-diethyl aniline and 5 g (42 mmol) of N-methyl imidazole. Upon completion of the addition the temperature is increased to 60° C. and allowed to stir for 12 hours to give the desired phosphorochloridite. Into the phosphorochloridite solution at ambient temperature is added 19.4 g (130 mmol) of N,N-diethyl aniline followed by the slow addition of a solution of 15 g (75 mmol) of PEG 200 and 3 g (30 mmol) of N-methylimidazole. This reaction mixture is allowed to stir at ambient temperature for 4 hours. The reaction mixture is then filtered and the filtrate is concentrated in vacuo to a light yellow oil.

$^{31}$P NMR (400 MHz) (Benzene-$d_6$) (ppm): 140-147

Alternatively:

B. The procedure of Example 13 is repeated using 16.9 g (123 mmol) of phosphorus trichloride, 1.4 g (14 mmol) of NMP, 59.0 g (250 mmol) of methyl 3-tert-butyl-4-hydroxyhydrocinnamate, 20.4 g (244 mmol) of MIM, 13.4 g (67 mmol) of polyethylene glycol 200 and a total of 175 g of toluene to give 68 g of a yellow, viscous syrup.

$^{31}$P NMR (400 MHz) (Benzene-$d_6$) (ppm): 143-145

Example 5

PEG 300 bis[di(2-tert-butyl-6-methylphenyl)]phosphite

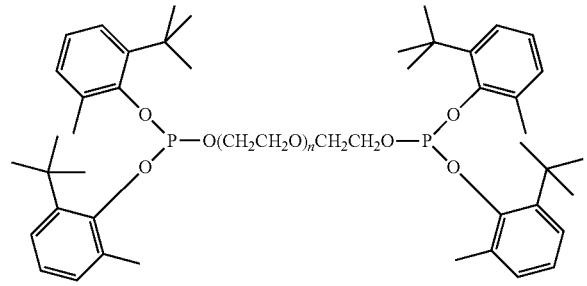

The procedure of Example 4 is repeated using 17.7 g (130 mmol) of phosphorus trichloride, 41.09 g (250 mmol) of 2-tert-butyl-6-methyl phenol, 22.5 g (75 mmol) of PEG 300, 56.7 g (380 mmol) of N,N-diethyl aniline, 8 g (72 mmol) of N-methylimidazole and a total of 150 g toluene to give a light yellow oil.

$^{31}$P NMR (400 MHz) (Benzene-$d_6$) (ppm): 161

Example 6

Tripropylene glycol bis[di(2-tert-butyl-6-methylphenyl)]phosphite

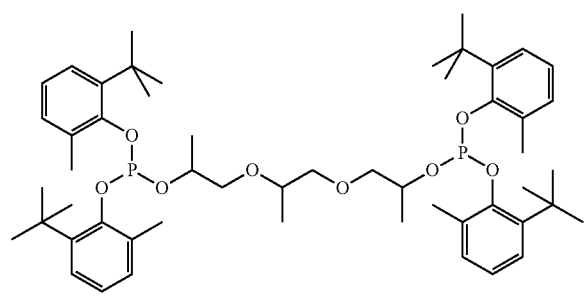

The procedure of Example 4 is repeated using 17.7 g (130 mmol) of phosphorus trichloride, 41.09 g (250 mmol) of 2-tert-butyl-6-methylphenol, 14.42 g (75 mmol) of tri(propylene glycol), 56.7 g (380 mmol) of N,N-diethyl aniline, 8 g (72 mmol) of N-methylimidazole and a total of 150 g toluene to give a very light yellow oil.

$^{31}$P NMR (300 MHz) (Benzene-$d_6$) (ppm): 160

Example 7

Triethylene glycol bis[di(2-sec-butylphenyl)]phosphite

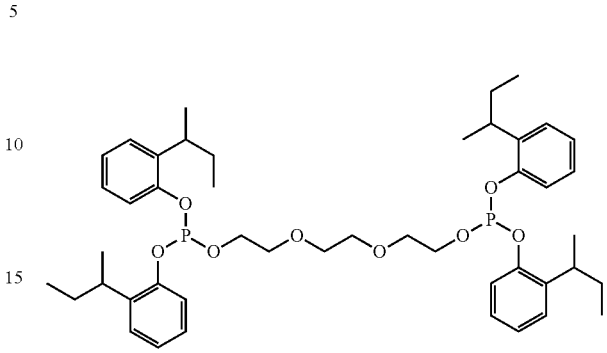

A. Into a mixture of 17.7 g (130 mmol) of phosphorus trichloride, 37.56 g (250 mmol) of ortho-sec-butyl phenol in 150 g of toluene is added dropwise a solution of 37.3 g (250 mmol) of N,N-diethyl aniline and 5 g (42 mmol) of N-methyl imidazole (MIM). Upon completion of the addition the temperature is increased to 60° C. and allowed to stir for 12 hours to give the desired phosphorochloridite. Into the phosphorochloridite solution at ambient temperature is added dropwise a solution 19.4 g (130 mmol) of N,N-diethyl aniline and 15.6 g (75 mmol) of triethyleneglycol and 3 g (30 mmol) of N-methylimidazole. This reaction mixture is allowed to stir at ambient temperature for 4 hours. The reaction mixture is filtered and the filtrate is concentrated in vacuo to a clear oil.

$^{31}$P NMR (400 MHz) (Benzene-$d_6$) (ppm): 145

Alternatively:

B. Into a solution of 17.2 g (125 mmol) of phosphorus trichloride in 100 mL of toluene is fed separately and concurrently 80 mL of 3.1 molar MIM in toluene and 80 mL 3.1 molar ortho-sec-butylphenol in toluene over 2 hours at 20-30° C. The reaction mass is held at temperature for 1 hour. A solution of 10.3 g (125 mmol) of MIM and 9.4 g (63 mmol) of triethylene glycol is added over 30 min at 25-35° C. The reaction mixture is filtered to remove salts and the filtrate concentrated in vacuo to yield 45.3 g of a colorless, viscous liquid.

$^{31}$P NMR (400MHz) (Benzene-$d_6$) (ppm): 145

Example 8

Triethylene glycol bis{di[2-tert-butyl-4-(methoxycarboxyprop-3-yl]phenyl)}phosphite

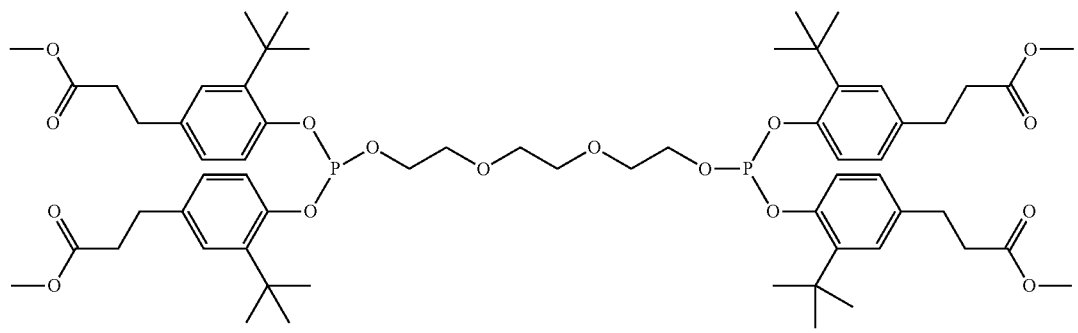

Into a mixture of 17.7 g (130 mmol) of phosphorus trichloride in 150 g of toluene at ambient temperature is added dropwise a solution of 37.3 g (250 mmol) of N,N-diethyl aniline and 5 g (42 mmol) of N-methyl imidazole and 19 g (130 mmol) of methyl 3-tert-butyl-4-hydroxyhydrocinnamate. Upon completion of the addition the temperature is increased to 60° C. and allowed to stir for 12 hours to give the desired phosphorochloridite. Into the phosphorochloridite solution at ambient temperature is added dropwise a solution 19.4 g (130 mmol) of N,N-diethyl aniline followed by a solution of 15 g (75 mmol) of triethylene glycol and 3 g (30 mmol) of N-methylimidazole. This reaction mixture is allowed to stir at ambient temperature for 4 hours. The reaction mixture is then filtered and the filtrate is concentrated in vacuo to yield a light yellow oil $^{31}$P NMR (400 MHz) (Benzene-d$_6$) (ppm): 145

Example 9

Triethylene glycol bis[di(2-tert-buty-6-methylphenyl)]phosphite

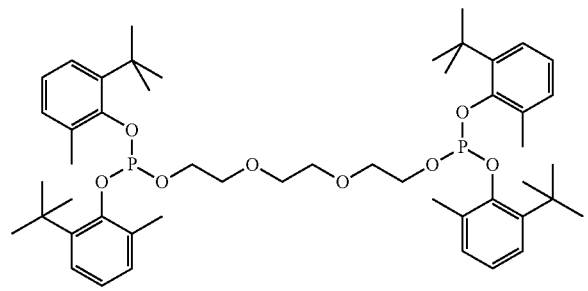

Into a mixture of 17.7 g (130 mmol) of phosphorus trichloride, 41.1 g (250 mmol) of 2-t-butyl-6-methylphenol in 150 g of toluene at ambient temperature is added dropwise 15 g (180 mmol) of N,N-diethyl aniline. Upon completion of the addition the temperature is increased to 60° C. and allowed to stir for 12 hours to give the desired phosphorochloridite. Into the phosphorochloridite solution at ambient temperature is added dropwise a solution 11.3 g (75 mmol) of N-methylimidazole followed by a solution of 11.3 g (75 mmol) of triethylene glycol. The reaction mixture is allowed to stir at ambient temperature for 4 hours. The reaction mixture is then filtered and the filtrate is concentrated in vacuo to afford a light yellow oil.
$^{31}$P NMR (400 MHz) (Benzene-d$_6$) (ppm): 161

Example 10

Tetraethylene glycol bis[di(2-tert-butyl-6-methylphenyl)]phosphite

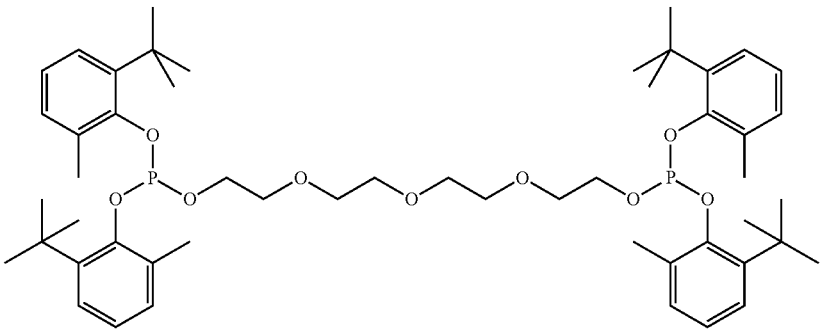
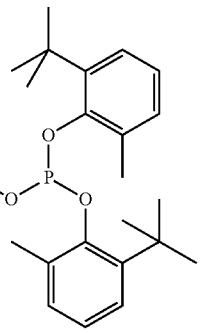

Into a solution of 17.7 g (126 mmol) of phosphorus trichloride in 100 g of toluene, a solution of 41.0 g (250 mmol) of 2-tert-butyl-6-methylphenol and 20.6 g (250 mmol) of 1-methylimidazole (MIM) in 70 g of toluene is added dropwise at 20-30° C. over 2 hours while under a nitrogen purge. The resulting mixture is held at 20-25° C. for an additional 30 minutes. A solution of 12.3 g (63 mmol) of tetraethyleneglycol and 10.3 g (122 mmol) of MIM is added dropwise over 30 minutes. The mixture is held for an additional hour. The reaction mixture is filtered and the filtrate is concentrated in vacuo at 70-75° C. to give a pale yellow, viscous syrup.
$^{31}$P NMR (400 MHz) (Benzene-d$_6$) (ppm): 160

Example 11

Triethylene glycol bis[di(2-tert-butyphenyl)]phosphite

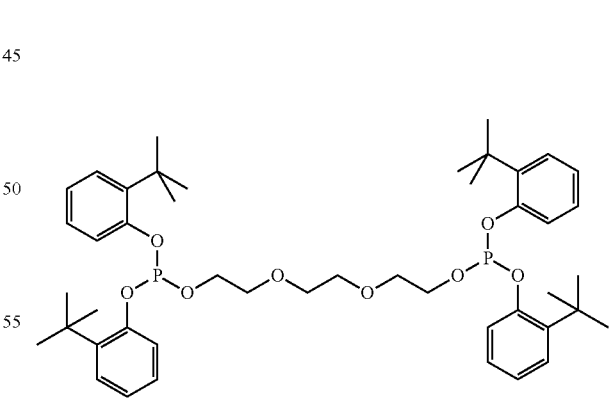

The procedure of Example 10 is repeated using 17.5 g (125 mmol) of phosphorus trichloride, 37.6 g (250 mmol) of 2-tert-butylphenol, 7.4 g (49 mmol) of triethylene glycol, a total of 30.2 g (370 mmol) of MIM and a total of 175 g of toluene to give a yellow, viscous syrup.
$^{31}$P NMR (400 MHz) (Benzene-d$_6$) (ppm): 146

Example 12

Triethylene glycol bis{di[2,5-di-tert-butyl-4-(methoxycarboxyprop-3-yl]phenyl)}phosphite

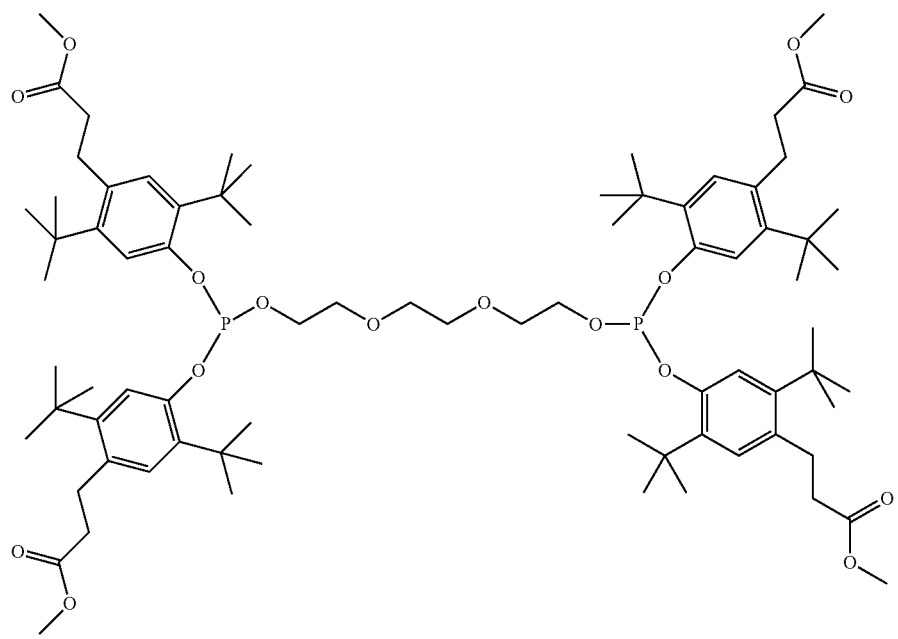

The procedure of Example 10 is repeated using 17.1 g (125 mmol) of phosphorus trichloride, 73.2 g (250 mmol) of methyl 3,6-di-tert-butyl-4-hydroxyhydrocinnamate, 9.4 g (63 mmol) of triethylene glycol, 31.2 g (380 mmol) of MIM and 205 g of toluene to give 55 g of a viscous, colorless liquid.

$^{31}$P NMR (400 MHz) (Benzene-$d_6$) (ppm): 153

Example 13

PEG 200/diethylene glycol bis{di[2-t-butyl-4-(methoxycarboxyprop-3-yl)phenyl]}phosphite Into a solution of 15.8 g (115 mmol) of phosphorus trichloride in 50 g of toluene and 1.3 g (13 mmol) of N-methyl-2-pyrrolidone (NMP), a solution of 55.5 g (235 mmol) of methyl 3-tert-butyl-4-hydroxyhydrocinnamate in 125 g of toluene is added dropwise at 40-50° C. over 3 hours while under a nitrogen purge. The resulting mixture is held at 45-50° C. for an additional 4 hours and 10 g (120 mmol) of MIM is added. A solution of 6.7 g (33 mmol) of polyethylene glycol 200, 3.6 g (34 mmol) of diethylene glycol and 10.4 g (124 mmol) of MIM is added dropwise over 20 minutes. The mixture is held for an additional hour. The reaction mixture is filtered and the filtrate is concentrated in vacuo at 70-75° C. to give 63 g of yellow, viscous syrup.

$^{31}$P NMR (400 MHz) (Benzene-$d_6$) (ppm): 143-145

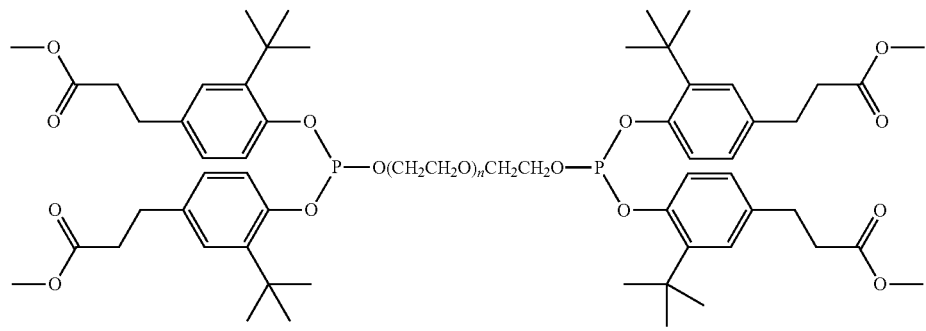

Example 14

Tetraethylene glycol bis[di(2-sec-butylphenyl)]phosphite

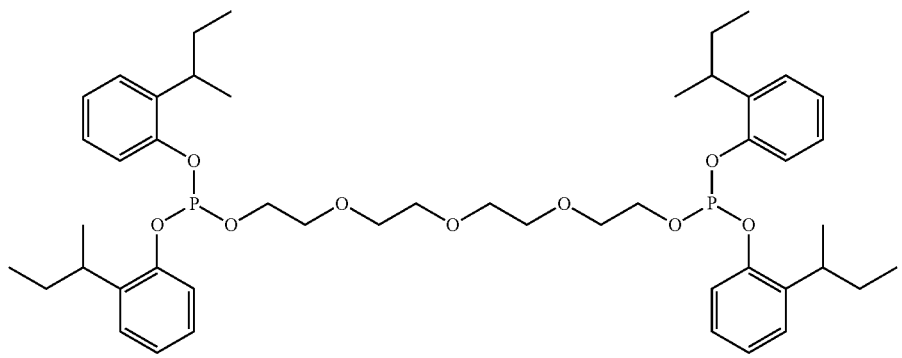

The procedure of Example 7B is repeated using 17.4 g (127 mmol) of phosphorus trichloride, 37.6 g (250 mmol) of 2-sec-butylphenol, 12.1 g (62 mmol) of tetraethylene glycol, 30.7 g (375 mmol) of MIM, and a total of 260 ml of toluene to give 44 g of an almost colorless, viscous liquid.

$^{31}$P NMR (400 MHz) (Benzene-$d_6$) (ppm): 145

Example 15

PEG 200 bis[di(2-sec-butylphenyl)]phosphite

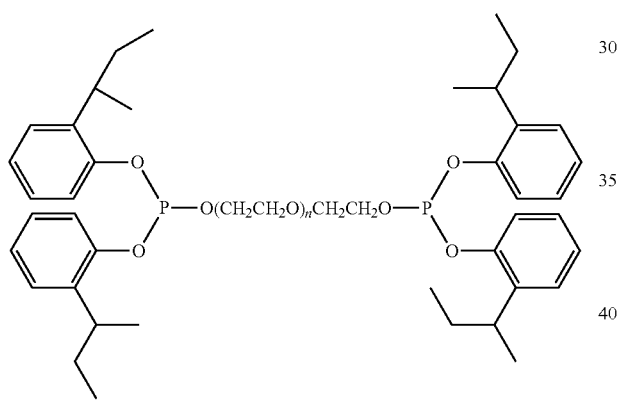

The procedure of Example 7b is repeated using 17.4 g (127 mmol) of phosphorus trichloride, 37.6 g (250 mmol) of 2-sec-butylphenol, 12.6 g (63 mmol) of PEG 200, 30.7 g (375 mmol) of MIM, and a total of 260 ml of toluene to give 43.5 g of a colorless, viscous liquid.

$^{31}$P NMR (400 MHz) (Benzene-$d_6$) (ppm): 142-144

Example 16

Mixture of triethylene glycol 2-sec-butylphenyl bis and tris phosphites

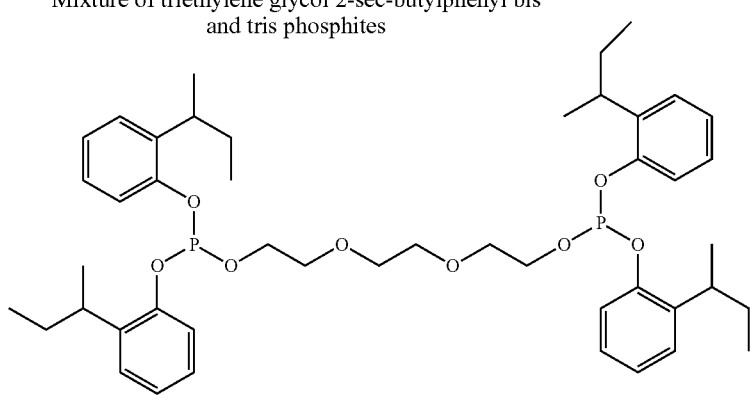

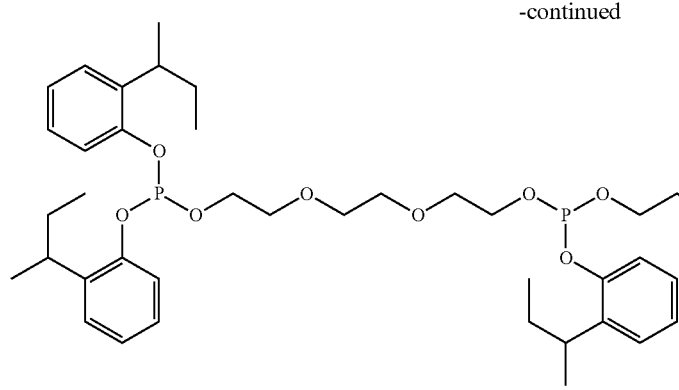

To an inerted glass reactor attached to a caustic scrubber, charged 430.6 g (2.866 mol) of o-sec-butylphenol. While cooling to 5° C., added 14.7 g (0.179 mol) of N-methylimidazole. Added 246.0 g (1.791 mol) of phosphorus trichloride dropwise over 3 hours maintaining the reactor temperature at 10-15° C. Upon completion of the addition, the reaction is held at 10-15° C. for 12 hours. The resulting phosphorochloridite mixture is warmed to 20° C. and sparged with nitrogen over 3 hours. To the resulting solution is charged 68.4 g of n-heptane followed by slowly adding in over 2 hours a premixed solution of 188.3 g (1.254 mol) of triethyleneglycol and 205.9 g (2.508 mol) of N-methylimidazole maintaining the reactor temperature at 30-35° C. Upon completion of the addition the temperature is increased to 90° C. and the bottom amine hydrochloride layer is split. The mixture is cooled to 20° C. while charging 234 g of n-heptane. The batch is vacuum filtered and the solvent removed in vacuo to yield a light yellowish oil.

$^{31}$P NMR (400 MHz) (Benzene-$d_6$) (ppm): 152.6, 147.5, 144.8, 142.5.

The tris-phenol phosphites are also present in the mixtures to a certain degree. In this case, tris-o-sec-butyl phosphite.

Higher analogues, for instance tetra or penta phosphites may also be prepared. The tetra phosphite obtainable with these reagents is:

The tetra phosphite is also present in this mixture to a certain degree.

The bis, tris and tetra phosphites will exist as a liquid mixture at room temperature and pressure.

Example 17

Liquid Phosphite Mixtures

Examples 1-15 are repeated employing a phenol:PCl$_3$ molar stoichiometry of about 1.6. This results in mixtures of the bis- and tris-phosphites as in present Example 16.

Application Examples

The following compounds are prepared as above:

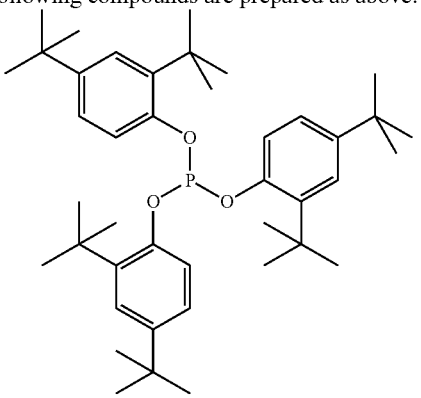

Phos1; solid; mp 182° C.; MW=647; % P=4.79

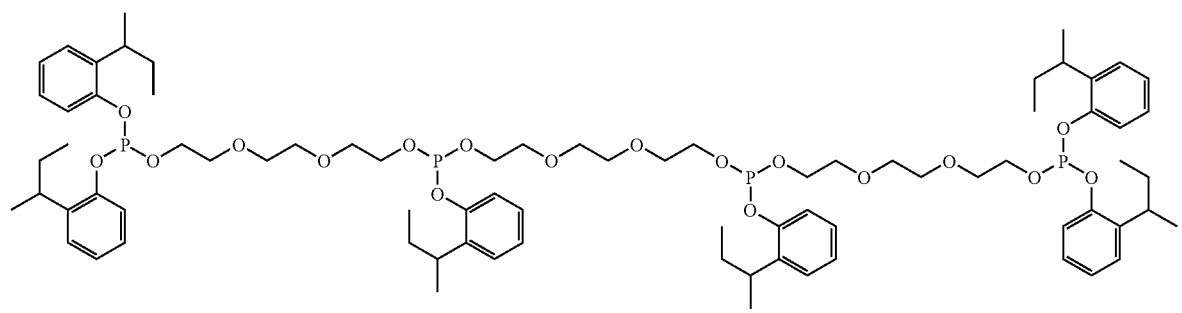

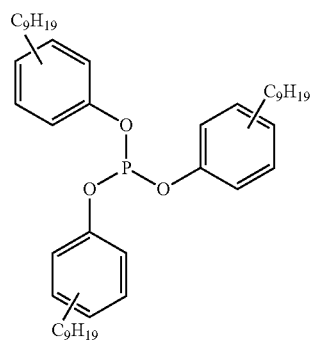
Phos2; pale yellow liquid; MW=689; % P=4.25
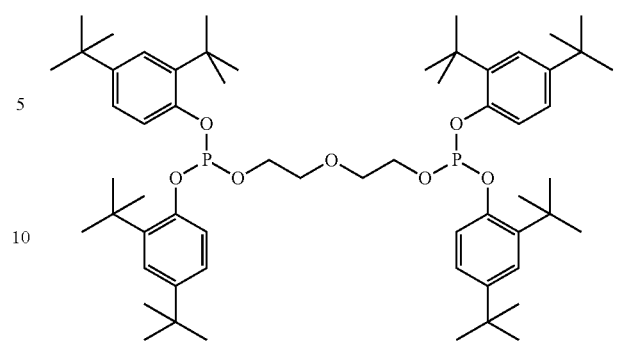
Phos3; colorless waxy solid; MW=987; % P=6.27
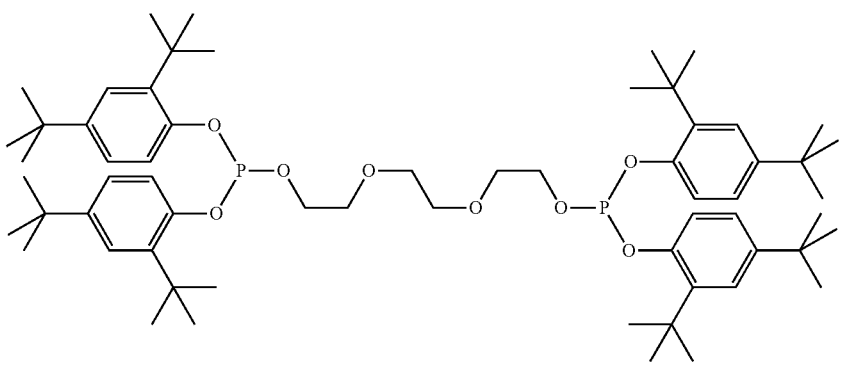
Phos4; colorless waxy solid; MW=1031; % P=6.01
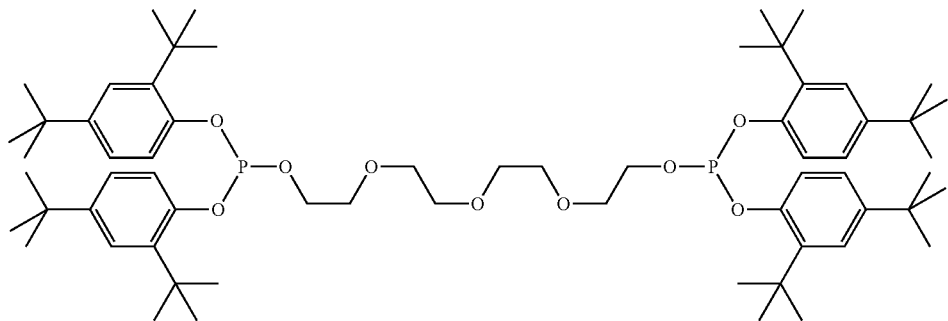
Phos5; colorless waxy solid; MW=1075; % P=5.76
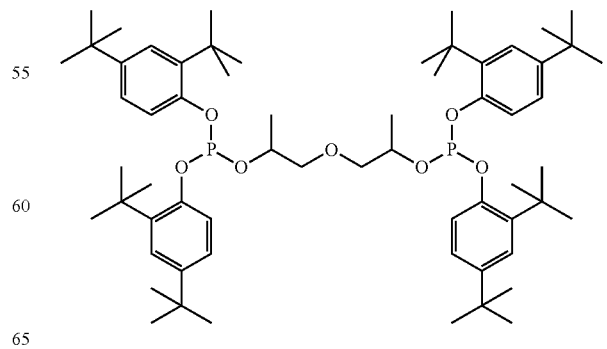
Phos6; colorless waxy solid; MW=1015; % P=6.10

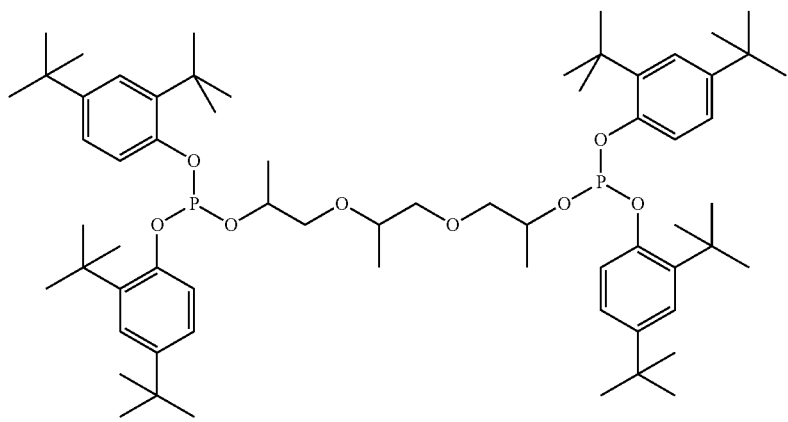
Phos7; colorless waxy solid; MW=1073; % P=5.77
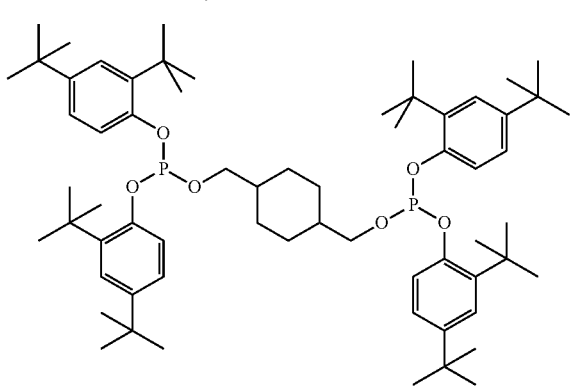
Phos8; colorless waxy solid; MW=1025; % P=6.04
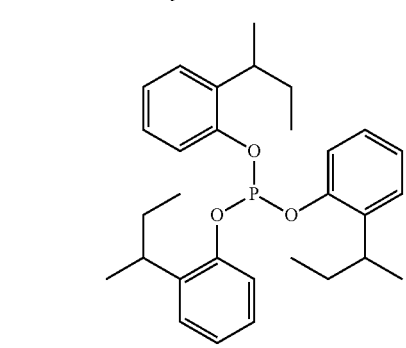
Phos9; colorless liquid; MW=479; % P=6.47
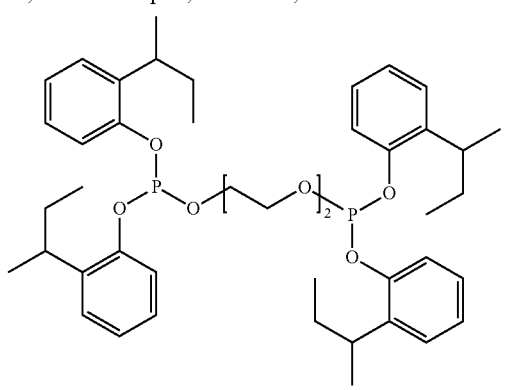
Phos10; colorless liquid; MW=763; % P=8.12
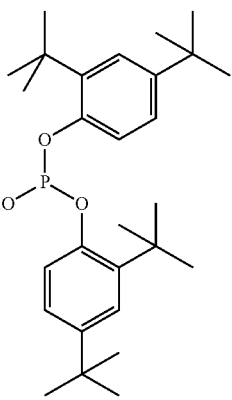
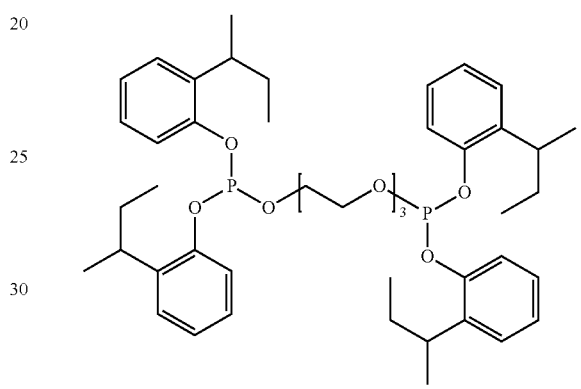
Phos11; colorless liquid; MW=807; % P=7.68
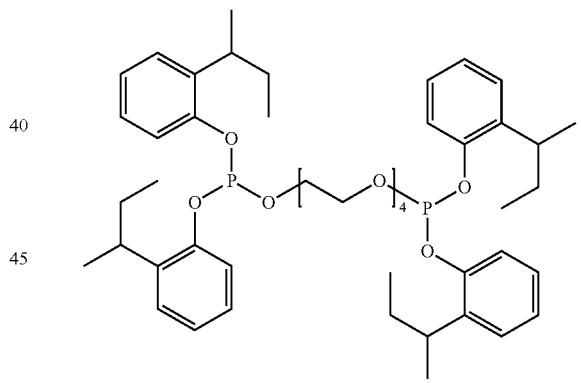
Phos12; colorless liquid; MW=851; % P=7.28
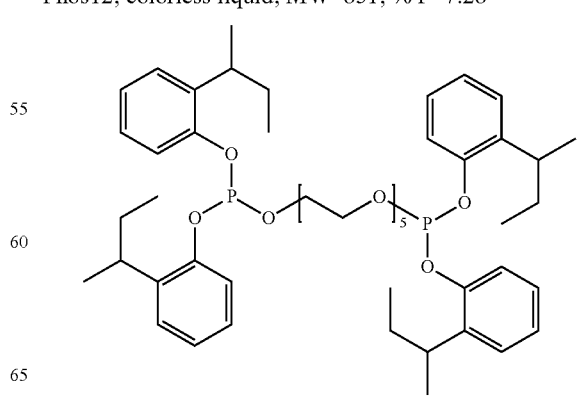
Phos13; colorless liquid; MW=895; % P=6.92

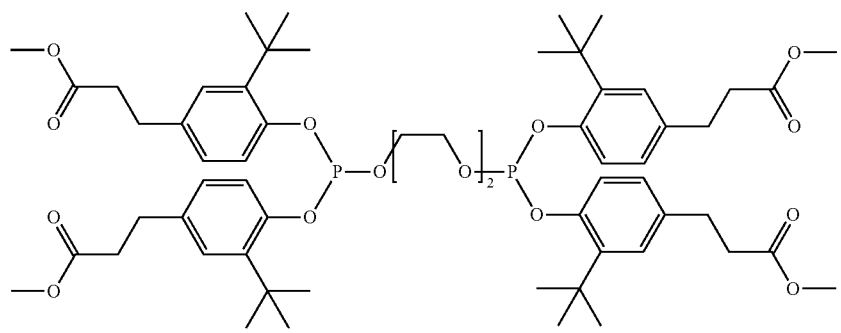
Phos14; colorless liquid; MW=1107; % P=5.59
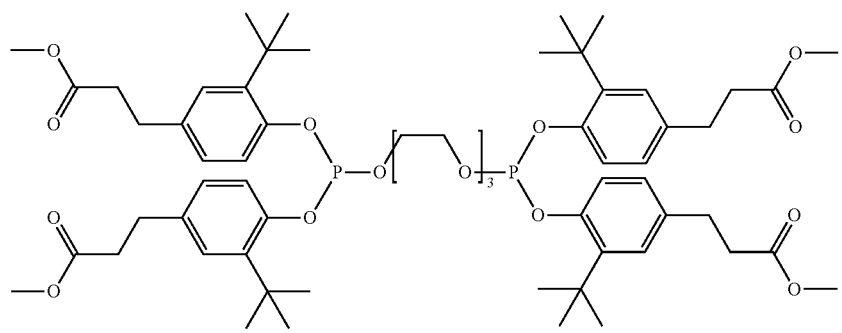
Phos15; colorless liquid; MW=1151; % P=5.38
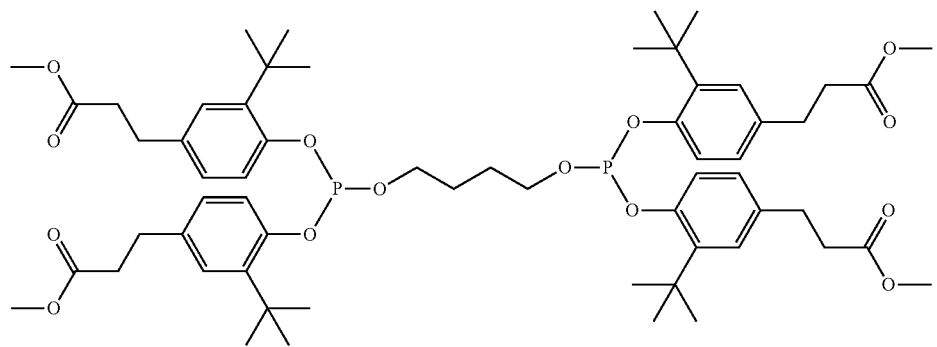
Phos16; colorless liquid; MW=1091; % P=5.68
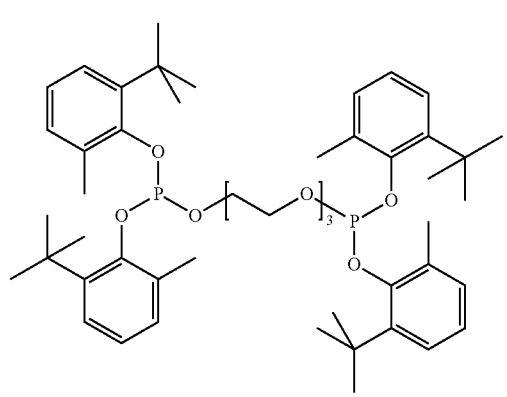
Phos17; colorless liquid; MW=863; % P=7.18
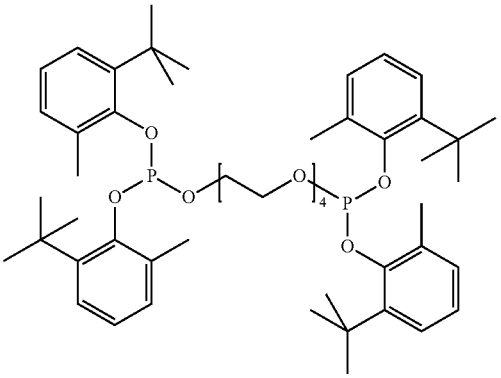
Phos18; colorless liquid; MW=907; % P=6.83

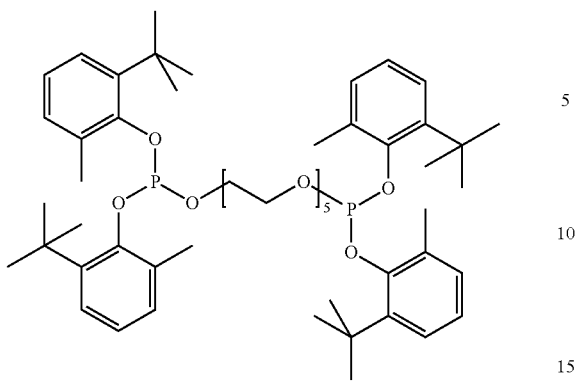
Phos19; colorless liquid; MW=951; % P=6.51
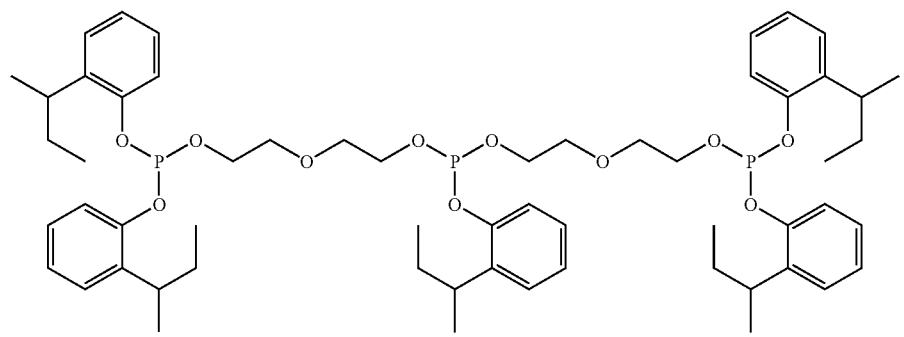
Phos20; colorless liquid; MW=1047; % P=8.87
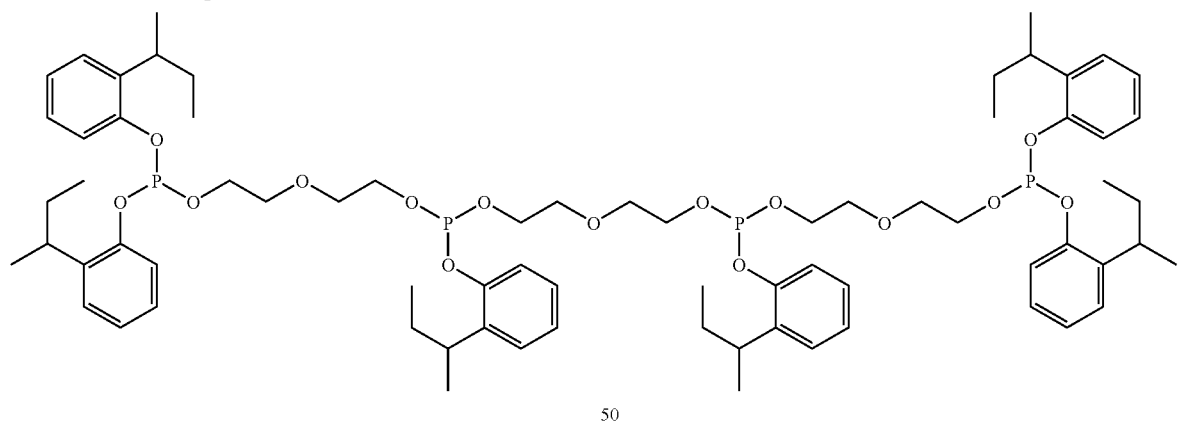
Phos21; colorless liquid; MW=1332; % P=9.30
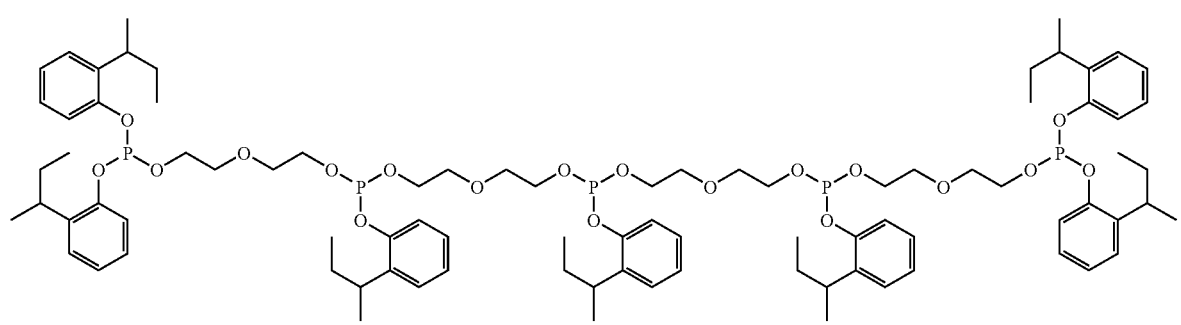
Phos22; colorless liquid; MW=1616; % P=9.58

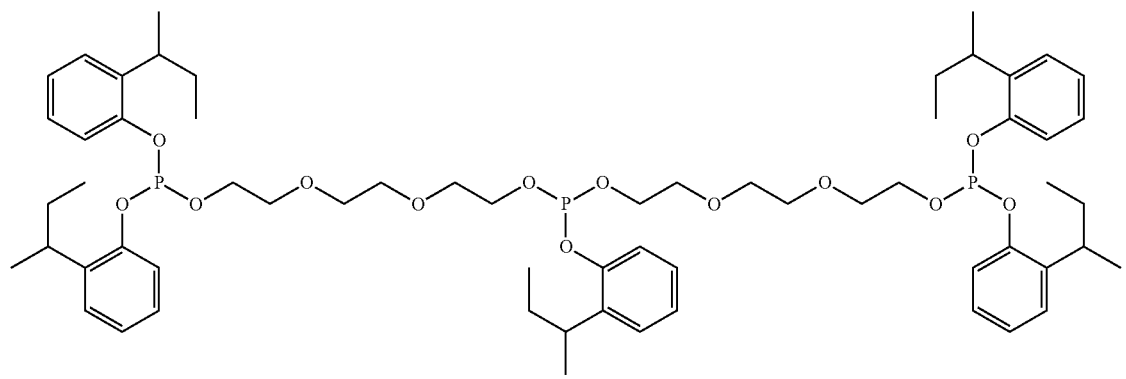
Phos23; colorless liquid; MW=1135; % P=8.18
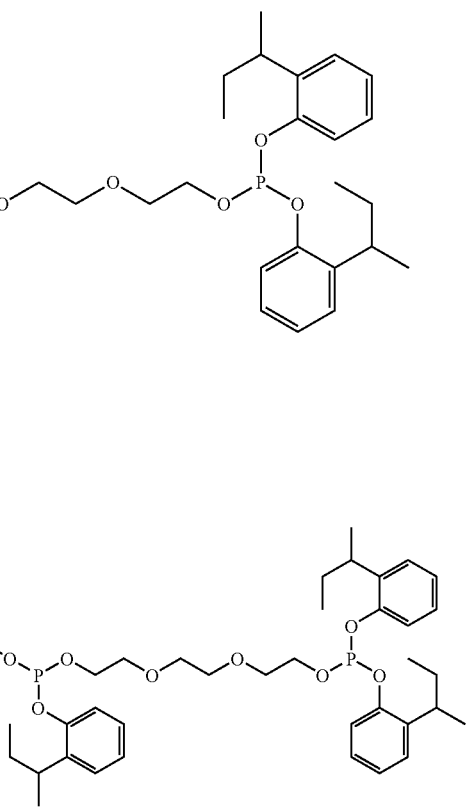
Phos24; colorless liquid; MW=1464; % P=8.46
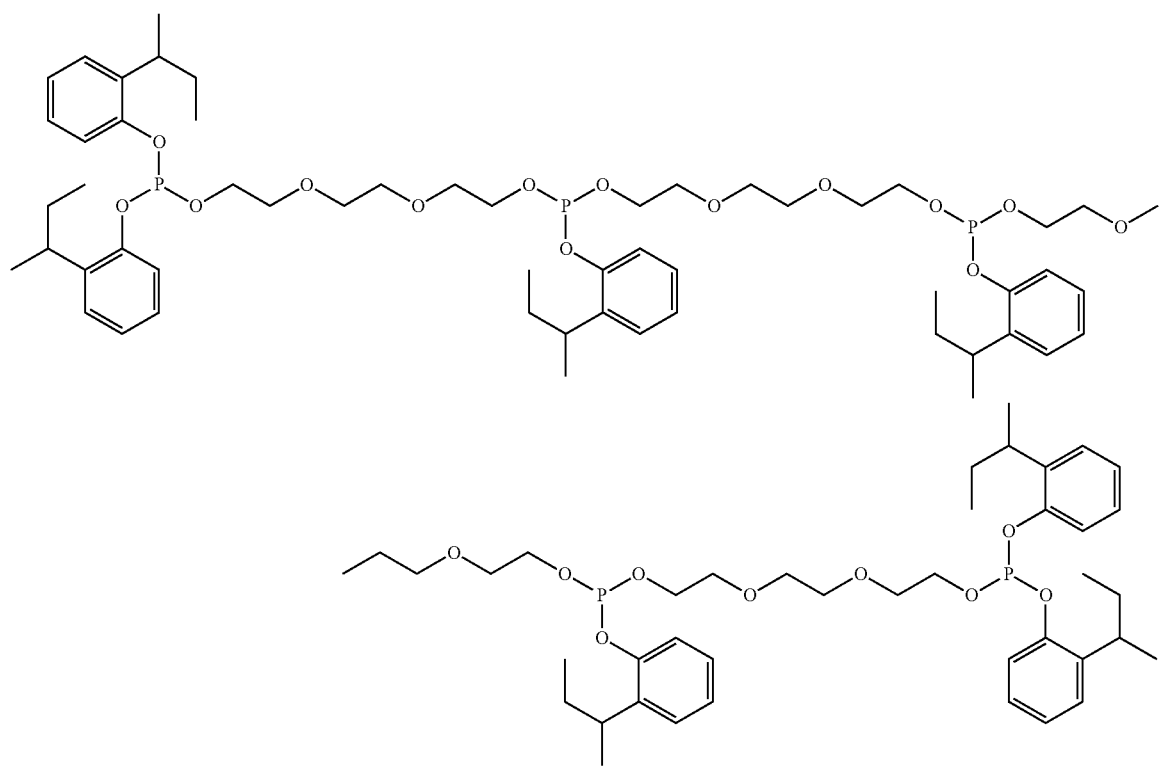
Phos25; colorless liquid; MW=1792; % P=8.64

Phos26; colorless liquid; mix of Phos9, Phos11, Phos23 and Phos24
Phos27; colorless liquid; mix of Phos9, Phos10, Phos20 and Phos21
Phos2-Phos25 are isolated by liquid chromatography.
Phos26 and Phos27 mixtures are prepared according to the present process with controlled stoichiometry. Phos26 is the mixture prepared according to present Example 16.

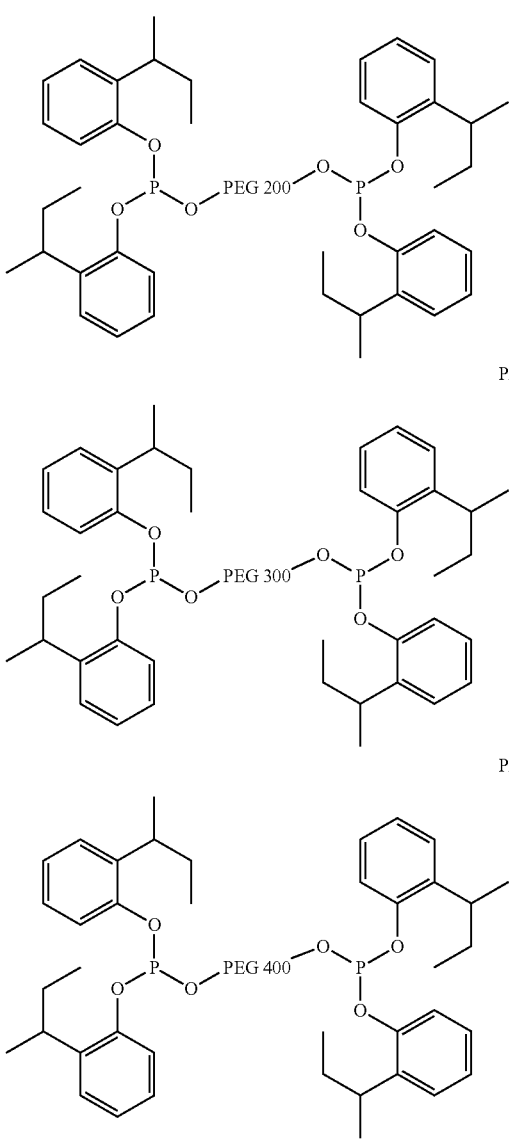

PhosA-PhosC are isolated by liquid chromatography.

The formulations in the Application Examples employ the following compounds:

AO1 is octadecyl 3-(3,5-di-tert-butyl-4-hydroxyphenyl) propionate (Irganoe 1076)

PPA1 is a binary mixture of a fluoroelastomer based polymer processing aid (DYNAMAR FX-5920A), and a high molecular weight polyethylene glycol Phos1 is tris(2,4-di-tert-butylphenyl) phosphite Phos2 is tris(nonylphenyl) phosphite Phos3-Phos27 (above)

Polymer Processing Experimental

A film grade ethylene/hexene metallocene catalyst based linear low density polyethylene (LL-1018; density=0.918 g/cm$^3$) essentially free of any stabilization additives is thoroughly blended with the base stabilization and the test additives using Turbula blenders or Kitchen-Aid mixers. The base stabilization in this example included 500 ppm of a phenolic antioxidant, denoted as AO1 (Irganox® 1076), and 800 ppm of a polymer processing aid, denoted as PPA1 (Dynamar FX-5920A). The phosphite test additives are added on a molar equivalent basis (typically 42.5 ppm phosphorus).

The formulations are initially melt compounded in a twin screw extruder at 190° C. under nitrogen; denoted as the zero pass extrusion. The resultant zero pass extrudate is then extruded multiple times a single screw extruder, fitted with a Maddock mixing section, at 260° C., open to air. Pellets samples of first, third and fifth pass extrudate are collected for additional testing.

The various pellet samples are tested for retention of the polymers original molecular weight by measuring the melt flow rate retention (according to ASTM-1238; 190° C.; low load at 2.16 kg; high load at 21.6 kg; as well as calculation of the melt flow ratio).

The color development observed during the multiple extrusion is measured (according to ASTM-1925) on compression molded plaques (125 mil; 3 minutes low pressure at 190° C., then 3 minutes high pressure at 190° C.; followed by 3 minutes of cooling at 10-15° C.).

The potential for color development after extrusion is assessed by exposing 10 mil compression molded plaques to oxides of nitrogen at 60° C. (according to ASTM-1925). A control experiment is run in parallel, at the same temperature, but without the oxides of nitrogen, in order to assess the color development associated with oxides of nitrogen vs. the color development associated with prolonged exposure to elevated temperatures (60° C.).

Polymer Processing Example 1

Using the polymer processing experimental procedure described above, the following formulations are evaluated. The concentration of the phosphite compounds are described in both parts per million in the final formulation (denoted as ppm Phos), as well as ppm P (as elemental phosphorus).

| Formula # | None | Phos 1 | Phos 2 | Phos 3 | Phos 6 | Phos 4 | Phos 5 | Phos 8 |
|---|---|---|---|---|---|---|---|---|
| ppm Phos | 0 | 888 | 1000 | 701 | 718 | 727 | 754 | 724 |
| ppm P | 0 | 42.5 | 42.5 | 42.5 | 42.5 | 42.5 | 42.5 | 42.5 |
| Melt Flow Rate; 190° C.; 2.16 kg | | | | | | | | |
| Zero | 0.92 | 0.92 | 0.97 | 0.90 | 0.94 | 0.95 | 0.95 | 0.97 |
| 1st | 0.89 | 0.92 | 0.95 | 0.93 | 0.96 | 0.95 | 0.94 | 0.96 |
| 3rd | 0.77 | 0.90 | 0.93 | 0.90 | 0.94 | 0.92 | 0.91 | 0.95 |
| 5th | 0.68 | 0.89 | 0.92 | 0.85 | 0.91 | 0.87 | 0.86 | 0.91 |

| Formula # | None | Phos 1 | Phos 2 | Phos 3 | Phos 6 | Phos 4 | Phos 5 | Phos 8 |
|---|---|---|---|---|---|---|---|---|
| Melt Flow Rate Data; 190° C.; 21.6 kg | | | | | | | | |
| Zero | 15.79 | 15.86 | 16.08 | 15.92 | 15.82 | 16.00 | 15.90 | 16.25 |
| 1st | 15.58 | 15.97 | 15.81 | 15.61 | 15.80 | 15.98 | 15.53 | 15.99 |
| 3rd | 15.03 | 15.85 | 15.92 | 15.48 | 16.01 | 15.99 | 15.75 | 16.27 |
| 5th | 14.56 | 16.03 | 16.12 | 15.76 | 16.35 | 15.74 | 15.47 | 16.22 |
| Melt Flow Ratio; 190° C.; 21.6/2.16 kg | | | | | | | | |
| Zero | 17.24 | 17.31 | 16.66 | 17.65 | 16.86 | 16.86 | 16.66 | 16.82 |
| 1st | 17.47 | 17.44 | 16.66 | 16.82 | 16.50 | 16.90 | 16.51 | 16.64 |
| 3rd | 19.60 | 17.56 | 17.05 | 17.17 | 17.01 | 17.37 | 17.33 | 17.17 |
| 5th | 21.53 | 17.97 | 17.46 | 18.53 | 17.89 | 18.19 | 18.07 | 17.79 |
| YI Color Data; C Illuminant; 2° Observer | | | | | | | | |
| Zero | 1.07 | −0.82 | −0.13 | 0.42 | −0.22 | −0.28 | −0.21 | −0.29 |
| 1st | 2.00 | 0.42 | 1.44 | 1.29 | 0.69 | 0.76 | 0.80 | 0.87 |
| 3rd | 3.12 | 4.10 | 3.38 | 2.40 | 2.68 | 2.32 | 2.03 | 1.85 |
| 5th | 4.47 | 6.19 | 4.40 | 4.03 | 5.68 | 4.06 | 3.21 | 3.70 |
| Gas Fade Aging; 60° C.; 1st Pass; | | | | | | | | |
| 0 Days | 1.31 | 1.17 | 1.23 | 1.21 | 1.09 | 1.11 | 1.23 | 1.14 |
| 7 Days | 5.91 | 3.44 | 1.65 | 2.14 | 2.22 | 2.72 | 2.38 | 2.54 |
| 14 Days | 9.78 | 5.36 | 2.28 | 3.37 | 3.32 | 4.42 | 4.77 | 4.20 |
| 21 Days | 13.52 | 8.96 | 3.63 | 4.40 | 5.31 | 5.30 | 8.35 | 5.11 |
| 28 Days | 13.13 | 8.37 | 3.94 | 5.12 | 5.96 | 5.64 | 8.07 | 5.57 |
| 35 Days | 11.18 | 7.84 | 4.25 | 5.59 | 6.75 | 5.98 | 8.15 | 6.15 |
| 42 Days | 10.87 | 7.66 | 4.74 | 5.62 | 7.02 | 6.14 | 8.19 | 6.20 |

As seen in the extrusion pass vs. melt flow rate retention table, the diol bridged phosphites provide good performance in comparison to both the traditional solid phosphite (Phos 1) as well as the liquid phosphite (Phos 2). Since the phosphorus concentrations are equivalent in each of the formulation comparisons, those skilled in the art should recognize the anticipated performance as measured by melt flow rate control from the diol bridged phosphites.

As can be seen in this extrusion pass vs. yellowness index color retention table, the liquid diol bridged phosphites provide good performance in comparison to both the traditional solid phosphite (Phos 1) as well as the liquid phosphite (Phos 2). Upon closer inspection, one can see that the liquid diol bridged phosphites provide at least equivalent, and more often better performance, as seen with Phos 3, Phos 4, Phos 5 and Phos 8. Since the phosphorus concentrations are equivalent in each of the comparisons, those skilled in the art should recognize the performance benefit derived from the liquid diol bridged phosphites.

As can be seen in this yellowness index color retention during exposure to oxides of nitrogen table, the liquid diol bridged phosphites provide superior performance in comparison to not including a phosphite as a stabilization component. They provide good performance in comparison to both the traditional solid phosphite (Phos 1) as well as the liquid phosphite (Phos 2).

Since the phosphorus concentrations are equivalent in each of the comparisons, those skilled in the art should recognize the overall performance benefit derived from the liquid diol bridged phosphites in comparison to Phos 1.

Polymer Processing Example 2

Using the polymer processing experimental procedure described above, the following formulations are evaluated. The concentration of the phosphite compounds are described in both parts per million in the final formulation (denoted as ppm Phos), as well as ppm P (as elemental phosphorus).

| Formula # | None | Phos 1 | Phos 2 | Phos 15 | Phos 10 | Phos 11 | Phos 17 |
|---|---|---|---|---|---|---|---|
| ppm Phos | 0 | 888 | 1000 | 790 | 523 | 554 | 592 |
| ppm P | 0 | 42.5 | 42.5 | 42.5 | 42.5 | 42.5 | 42.5 |
| Melt Flow Rate; 190° C.; 2.16 kg | | | | | | | |
| Zero | 0.97 | 0.96 | 0.96 | 0.93 | 0.95 | 0.94 | 0.94 |
| 1st | 0.93 | 0.96 | 0.97 | 0.92 | 0.95 | 0.95 | 0.95 |
| 3rd | 0.73 | 0.89 | 0.96 | 0.91 | 0.91 | 0.94 | 0.93 |
| 5th | 0.57 | 0.83 | 0.92 | 0.86 | 0.87 | 0.91 | 0.92 |
| Melt Flow Rate Data; 190° C.; 21.6 kg | | | | | | | |
| Zero | 15.67 | 15.47 | 15.67 | 15.35 | 15.47 | 15.27 | 15.41 |
| 1st | 15.72 | 15.59 | 15.63 | 15.35 | 15.49 | 15.37 | 15.38 |
| 3rd | 15.02 | 15.44 | 15.75 | 15.71 | 15.30 | 15.40 | 15.41 |
| 5th | 14.41 | 15.29 | 15.65 | 15.48 | 15.18 | 15.24 | 15.29 |
| Melt Flow Ratio; 190° C.; 21.6/2.16 kg | | | | | | | |
| Zero | 16.22 | 16.11 | 16.31 | 16.58 | 16.23 | 16.19 | 16.41 |
| 1st | 16.94 | 16.19 | 16.20 | 16.63 | 16.28 | 16.18 | 16.16 |
| 3rd | 20.57 | 17.37 | 16.48 | 17.18 | 16.82 | 16.41 | 16.58 |
| 5th | 25.41 | 18.50 | 16.96 | 17.97 | 17.44 | 16.79 | 16.68 |
| YI Color Data; C Illuminant; 2° Observer | | | | | | | |
| Zero | −0.17 | −0.32 | −0.97 | −1.08 | −0.97 | −0.74 | −0.81 |
| 1st | 2.46 | 0.97 | 0.43 | 0.01 | 0.00 | 0.15 | 0.56 |
| 3rd | 6.04 | 4.83 | 2.32 | 1.49 | 2.16 | 2.14 | 2.40 |
| 5th | 9.33 | 6.56 | 4.13 | 3.26 | 4.18 | 3.25 | 3.83 |
| Gas Fade Aging; 60° C.; 1st Pass; | | | | | | | |
| 0 Days | 1.32 | 1.35 | 1.25 | 1.36 | 1.48 | 1.34 | 1.37 |
| 7 Days | 3.35 | 2.26 | 1.65 | 3.19 | 1.55 | 1.57 | 1.94 |
| 14 Days | 6.47 | 3.08 | 2.32 | 4.26 | 2.98 | 3.37 | 3.72 |
| 21 Days | 8.76 | 3.96 | 2.95 | 4.69 | 4.48 | 5.11 | 4.94 |
| 28 Days | 10.05 | 4.40 | 3.03 | 4.73 | 4.70 | 5.27 | 4.65 |
| 35 Days | 10.12 | 4.64 | 3.38 | 4.70 | 4.86 | 5.15 | 4.19 |
| 42 Days | 9.89 | 4.23 | 3.60 | 4.62 | 4.87 | 5.12 | 4.90 |

As seen in the extrusion pass vs. melt flow rate retention table, the diol bridged phosphites provide good performance in comparison to both the traditional solid phosphite (Phos 1) as well as the liquid phosphite (Phos 2). Since the phosphorus concentrations are equivalent in each of the formulation comparisons, those skilled in the art should recognize the anticipated performance as measured by melt flow rate control from the diol bridged phosphites. Phos 11 is superior.

As can be seen in this extrusion pass vs. yellowness index color retention table, the liquid diol bridged phosphites provide good performance in comparison to both the traditional solid phosphite (Phos 1) as well as the liquid phosphite (Phos 2). Upon closer inspection, one can see that the liquid diol bridged phosphites provide equivalent, and typically better performance, as seen with Phos 11, Phos 15 and Phos 17. Since the phosphorus concentrations are equivalent in each of the comparisons, those skilled in the art should recognize the performance benefit derived from the liquid diol bridged phosphites.

As can be seen in this yellowness index color retention during exposure to oxides of nitrogen table, the liquid diol bridged phosphites provide superior performance in comparison to not including a phosphite as a stabilization component. They provide good performance in comparison to both the traditional solid phosphite (Phos 1) as well as the liquid phosphite (Phos 2).

Since the phosphorus concentrations are equivalent in each of the comparisons, those skilled in the art should recognize the overall performance benefit derived from the liquid diol bridged phosphites in comparison to Phos 1.

Polymer Processing Example 3

Using the polymer processing experimental procedure described above, the following formulations are evaluated. The concentration of the phosphite compounds are described in parts per million based on the final formulation, denoted as ppm Phos, as well as ppm P (elemental phosphorus).

As seen in the extrusion pass vs. melt flow rate retention table, the diol bridged phosphites provide good performance in comparison to both the traditional solid phosphite (Phos 1) as well as the liquid phosphite (Phos 2). Since the phosphorus concentrations are equivalent in each of the formulation comparisons, those skilled in the art should recognize the anticipated performance as measured by melt flow rate control from the diol bridged phosphites. Phos 19 is superior.

As can be seen in this extrusion pass vs. yellowness index color retention table, the liquid diol bridged phosphites provide good performance in comparison to both the traditional solid phosphite (Phos 1) as well as the liquid phosphite (Phos 2). Upon closer inspection, one can see that the liquid diol bridged phosphites provide equivalent, and typically better performance, as seen with Phos 12 and Phos 13. Since the phosphorus concentrations are equivalent in each of the comparisons, those skilled in the art should recognize the performance benefit derived from the liquid diol bridged phosphites.

As can be seen in this yellowness index color retention during exposure to oxides of nitrogen table, the liquid diol bridged phosphites provide superior performance in comparison to not including a phosphite as a stabilization component. They provide good performance in comparison to both the traditional solid phosphite (Phos 1) as well as the liquid phosphite (Phos 2).

Since the phosphorus concentrations are equivalent in each of the comparisons, those skilled in the art should recognize the overall performance benefit derived from the liquid diol bridged phosphites in comparison to Phos 1.

Polymer Processing Example 4

Using the polymer processing experimental procedure described above, the following formulations are evaluated.

| Formula # | None | Phos 1 | Phos 2 | Phos 13 | Phos 14 | Phos 18 | Phos 19 | Phos 12 |
|---|---|---|---|---|---|---|---|---|
| ppm Phos | 0 | 888 | 1000 | 614 | 760 | 622 | 653 | 584 |
| ppm P | 0 | 42.5 | 42.5 | 42.5 | 42.5 | 42.5 | 42.5 | 42.5 |
| Melt Flow Rate; 190° C.; 2.16 kg | | | | | | | | |
| Zero | 0.95 | 0.95 | 0.96 | 0.96 | 0.95 | 0.93 | 0.93 | 0.94 |
| 1st | 0.89 | 0.94 | 0.96 | 0.96 | 0.95 | 0.93 | 0.93 | 0.95 |
| 3rd | 0.73 | 0.89 | 0.95 | 0.94 | 0.92 | 0.91 | 0.93 | 0.92 |
| 5th | 0.63 | 0.86 | 0.90 | 0.90 | 0.87 | 0.88 | 0.91 | 0.90 |
| Melt Flow Rate Data; 190° C.; 21.6 kg | | | | | | | | |
| Zero | 15.48 | 15.30 | 15.57 | 15.52 | 15.41 | 15.16 | 15.21 | 15.28 |
| 1st | 15.22 | 15.39 | 15.58 | 15.52 | 15.36 | 15.24 | 15.33 | 15.36 |
| 3rd | 14.30 | 15.35 | 15.55 | 15.50 | 15.35 | 15.23 | 15.33 | 15.27 |
| 5th | 13.55 | 15.12 | 15.48 | 15.32 | 15.19 | 15.07 | 15.28 | 15.17 |
| Melt Flow Ratio; 190° C.; 21.6/2.16 kg | | | | | | | | |
| Zero | 16.29 | 16.16 | 16.20 | 16.14 | 16.30 | 16.39 | 16.33 | 16.21 |
| 1st | 17.03 | 16.38 | 16.18 | 16.12 | 16.15 | 16.42 | 16.43 | 16.25 |
| 3rd | 19.52 | 17.15 | 16.41 | 16.44 | 16.74 | 16.73 | 16.48 | 16.65 |
| 5th | 21.34 | 17.52 | 17.13 | 17.11 | 17.56 | 17.13 | 16.86 | 16.78 |
| YI Color Data; C Illuminant; 2° Observer | | | | | | | | |
| Zero | −0.23 | −0.86 | −0.79 | −1.45 | −1.15 | −0.77 | −0.61 | −0.77 |
| 1st | 0.55 | −0.01 | 0.00 | −0.90 | −0.55 | −0.07 | 0.01 | 0.00 |
| 3rd | 1.70 | 0.97 | 1.19 | 0.25 | 1.28 | 1.12 | 0.86 | 1.09 |
| 5th | 2.99 | 1.99 | 2.24 | 1.43 | 2.21 | 1.65 | 2.97 | 1.96 |
| Gas Fade Aging; 60° C.; 1st Pass; | | | | | | | | |
| 0 Days | 1.12 | 1.05 | 1.10 | 1.03 | 0.95 | 1.03 | 1.03 | 1.09 |
| 7 Days | 3.99 | 2.01 | 1.39 | 1.37 | 3.17 | 1.67 | 2.01 | 2.22 |
| 14 Days | 6.62 | 2.74 | 2.00 | 2.70 | 4.50 | 2.48 | 3.51 | 3.92 |
| 21 Days | 8.70 | 3.33 | 2.63 | 5.07 | 4.65 | 2.85 | 4.30 | 4.54 |
| 28 Days | 8.87 | 3.62 | 3.04 | 6.02 | 4.68 | 3.25 | 4.69 | 4.66 |
| 35 Days | 9.64 | 3.86 | 3.25 | 6.38 | 4.79 | 3.44 | 4.90 | 4.88 |
| 42 Days | 9.01 | 3.92 | 3.33 | 6.19 | 4.57 | 3.40 | 4.85 | 4.31 |

The concentration of the phosphite compounds are described in parts per million based on the final formulation, denoted as ppm Phos, as well as ppm P (elemental phosphorus).

| Formula # | None | Phos 1 | Phos 2 | Phos 11 | Phos 26 | Phos 27 |
|---|---|---|---|---|---|---|
| ppm Phos | 0 | 888 | 1000 | 554 | 554 | 523 |
| ppm P | 0 | 42.5 | 42.5 | 42.5 | 42.5 | 42.5 |
| Melt Flow Rate; 190° C.; 2.16 kg | | | | | | |
| Zero | 0.91 | 0.91 | 0.90 | 0.89 | 0.92 | 0.90 |
| 1st | 0.88 | 0.91 | 0.90 | 0.90 | 0.92 | 0.90 |
| 3rd | 0.82 | 0.89 | 0.90 | 0.89 | 0.91 | 0.89 |
| 5th | 0.75 | 0.87 | 0.87 | 0.86 | 0.86 | 0.86 |
| Melt Flow Rate Data; 190° C.; 21.6 kg | | | | | | |
| Zero | 14.59 | 14.69 | 14.73 | 14.79 | 14.89 | 14.83 |
| 1st | 14.43 | 14.84 | 14.80 | 14.85 | 14.88 | 14.75 |
| 3rd | 14.17 | 14.74 | 14.82 | 14.90 | 15.01 | 14.79 |
| 5th | 13.76 | 14.75 | 14.92 | 14.87 | 14.92 | 14.79 |
| Melt Flow Ratio; 190° C.; 21.6/2.16 kg | | | | | | |
| Zero | 16.05 | 16.15 | 16.40 | 16.65 | 16.27 | 16.48 |
| 1st | 16.36 | 16.24 | 16.50 | 16.57 | 16.24 | 16.44 |
| 3rd | 17.32 | 16.51 | 16.47 | 16.84 | 16.50 | 16.66 |
| 5th | 18.37 | 16.90 | 17.15 | 17.25 | 17.26 | 17.14 |
| YI Color Data; C Illuminant; 2° Observer | | | | | | |
| Zero | −0.70 | −0.44 | −1.04 | −1.56 | −1.57 | −1.73 |
| 1st | 0.14 | 0.84 | 0.18 | −0.72 | −0.83 | −1.08 |
| 3rd | 1.16 | 2.14 | 1.94 | 0.43 | 0.52 | −0.13 |
| 5th | 2.23 | 3.40 | 3.31 | 1.83 | 1.76 | 1.13 |
| Gas Fade Aging; 60° C.; 1st Pass; | | | | | | |
| 0 | 1.25 | 1.40 | 1.39 | 1.39 | 1.17 | 1.17 |
| 7 | 4.74 | 3.22 | 1.58 | 1.59 | 1.57 | 1.56 |
| 14 | 8.32 | 4.52 | 2.57 | 3.09 | 4.11 | 3.24 |
| 21 | 10.46 | 5.37 | 3.71 | 5.95 | 6.37 | 5.46 |
| 28 | 10.17 | 6.16 | 3.82 | 6.04 | 5.54 | 5.23 |
| 35 | 10.06 | 5.28 | 4.45 | 5.81 | 5.31 | 5.00 |
| 42 | 9.05 | 4.83 | 4.76 | 5.63 | 5.17 | 4.90 |

As seen in the extrusion pass vs. melt flow rate retention table, the diol bridged phosphites provide good performance in comparison to both the traditional solid phosphite (Phos 1) as well as the liquid phosphite (Phos 2). Since the phosphorus concentrations are equivalent in each of the formulation comparisons, those skilled in the art should recognize the anticipated performance as measured by melt flow rate control from the diol bridged phosphites. Phos 27 is superior.

As can be seen in this extrusion pass vs. yellowness index color retention table, the liquid diol bridged phosphites provide good performance in comparison to both the traditional solid phosphite (Phos 1) as well as the liquid phosphite (Phos 2). Upon closer inspection, one can see that the liquid diol bridged phosphites provide equivalent, and typically better performance, as seen with Phos 11, Phos 26 and Phos 27. Since the phosphorus concentrations are equivalent in each of the comparisons, those skilled in the art should recognize the performance benefit derived from the liquid diol bridged phosphites.

As can be seen in this yellowness index color retention during exposure to oxides of nitrogen table, the liquid diol bridged phosphites provide superior performance in comparison to not including a phosphite as a stabilization component. They provide good performance in comparison to both the traditional solid phosphite (Phos 1) as well as the liquid phosphite (Phos 2).

Since the phosphorus concentrations are equivalent in each of the comparisons, those skilled in the art should recognize the overall performance benefit derived from the liquid diol bridged phosphites in comparison to Phos 1.

Viscosity Measurements

The shear viscosity of the various phosphorus based stabilizers is measured to assess the flow properties. The flowability of these materials is an extremely important consideration when taking into consideration how stabilizing additives are introduced into the manufacturing process during the production. The ability to use liquids can be highly valued, due to the improved accuracy of introducing and mixing of the additives into the polymer matrix, as long as the liquid additives have the appropriate viscosity profile. In order to assess this, an AR2000N rheometer, made by TA Instruments, Inc., is used for these measurements. The rheometer is fitted with a 40 mm 2° steel cone and Peltier plate. A shear stress of 10 Pascal is applied, along with a temperature ramp of 2° C./minute over a temperature range of 0° C. to 100° C. during the viscosity measurements. The viscosity profiles are shown in the table below.

It is preferred to have a material that can be pumped and stored as a liquid at room temperature. It is more preferred to viscosity close to the industry benchmarks, such as TNPP, where there is proven track record of being able to store, handle and pump the material through various pipes and fittings at temperatures conventionally used at polymer production facilities. It is most preferred to have a viscosity between around 0.25 Pascal·second at 60° C. to about 0.08 Pascal·second at 80° C.

The liquid diol bridged phosphites of the present invention based on 2-sec-butylphenol (2sbp) are much less viscous than the industry benchmark liquid phosphite Phos 2 (TNPP). These 2sbp based diol bridged phosphites are also much less viscous than their respective diol bridged phosphite counterparts based on other phenols, such as 2,4-di-t-butylphenol (2,4-dtbp) and 2-methly-6-t-butylphenol (mtbp). The lower viscosity of these 2sbp based diol bridged phosphites allows for greater ease of storage, handling and pumping at temperatures conventionally used at polymer production facilities.

| Viscosity Table | | | | | | |
|---|---|---|---|---|---|---|
| Sample | Viscosity (mPa · s) | | | | | |
| ID | 2° C. | 20° C. | 40° C. | 60° C. | 80° C. | 100° C. |
| Phos 1 | solid | solid | solid | solid | solid | solid |
| Phos 2 | 139.80 | 10.82 | 1.252 | 0.2539 | 0.0791 | 0.03354 |
| Phos 3 | >3000 | >3000 | >3000 | 602.90 | 9.161 | 0.7117 |
| Phos 4 | >3000 | >3000 | >3000 | 65.76 | 2.661 | 0.3756 |
| Phos 5 | >3000 | >3000 | 2792 | 28.24 | 1.792 | 0.3166 |
| Phos A | >3000 | >3000 | 1600 | 18.80 | 1.242 | 0.2238 |
| Phos B | >3000 | >3000 | 102.6 | 4.886 | 0.6539 | 0.1696 |
| Phos C | >3000 | 802.3 | 22.07 | 2.127 | 0.4289 | 0.1348 |
| Phos 6 | >3000 | >3000 | >3000 | 448.6 | 7.842 | 0.6356 |
| Phos 9 | 1.486 | 0.2439 | 0.05809 | 0.02191 | 0.0109 | 0.0066 |
| Phos 10 | 13.20 | 1.433 | 0.2401 | 0.07046 | 0.02919 | 0.01514 |
| Phos 11 | 7.661 | 0.9645 | 0.1842 | 0.05884 | 0.02581 | 0.01397 |
| Phos 12 | 4.871 | 0.6783 | 0.1447 | 0.04945 | 0.02263 | 0.01259 |

Viscosity Table

| Sample ID | Viscosity (mPa·s) | | | | | |
|---|---|---|---|---|---|---|
| | 2° C. | 20° C. | 40° C. | 60° C. | 80° C. | 100° C. |
| Phos 13 | 4.266 | 0.6171 | 0.1363 | 0.0485 | 0.02274 | 0.01256 |
| Phos 14 | >3000 | 302 | 9.737 | 1.103 | 0.2579 | 0.09058 |
| Phos 15 | >3000 | 121 | 5.545 | 0.8043 | 0.2099 | 0.0753 |
| Phos 17 | >3000 | 1154 | 14.53 | 0.9997 | 0.1826 | 0.05827 |
| Phos 19 | >3000 | 560.7 | 10.04 | 0.8626 | 0.1757 | 0.05932 |
| Phos 26 | 14.59 | 1.85 | 0.349 | 0.1092 | 0.04709 | 0.02511 |
| Phos 27 | 17.51 | 2.023 | 0.3535 | 0.1078 | 0.04595 | 0.0246 |

The invention claimed is:

1. A stabilizer mixture comprising oxyalkylene bridged bis- and tris-phosphite esters of formulae I and II

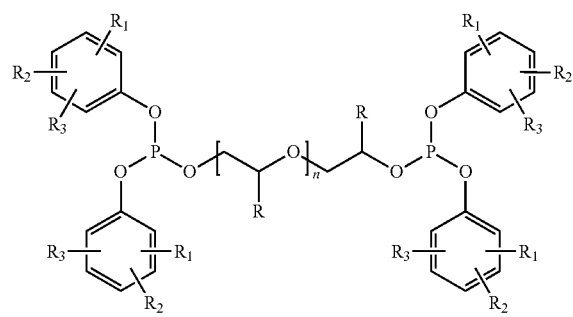
(I)

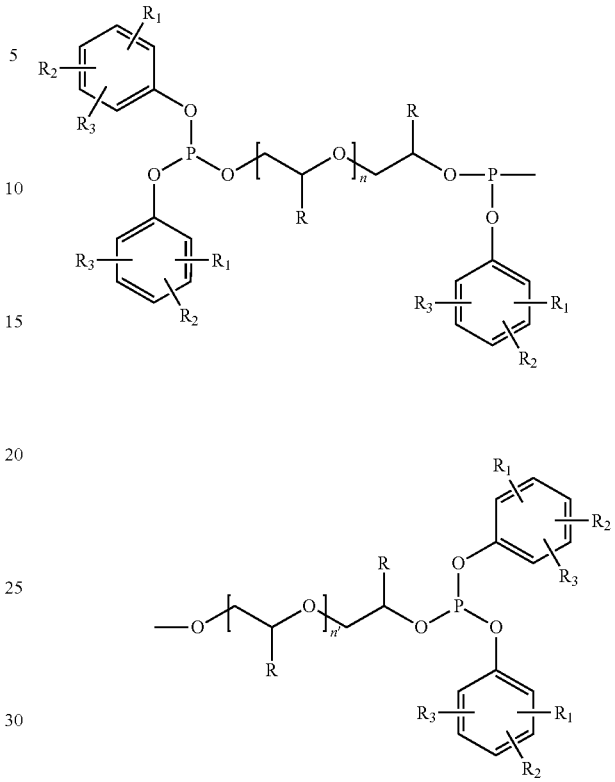
(II)

where
R is hydrogen or methyl,
n and n' are independently an integer from 1 to 45 and
$R_1$, $R_2$ and $R_3$ are each independently hydrogen, straight or branched chain alkyl of 1 to 12 carbon atoms, phenylalkyl of 7 to 9 carbon atoms, phenylalkyl of 7 to 9 carbon atoms substituted on the phenyl ring by one to three straight or branched chain alkyl of 1 to 12 carbon atoms or $R_1$, $R_2$ and $R_3$ are each independently —$(CH_2)_k$—$COOR_4$ where k is 0, 1 or 2 and $R_4$ is hydrogen or straight or branched chain alkyl of 1 to 20 carbon atoms.

2. A mixture according to claim 1 comprising esters formulae I and II

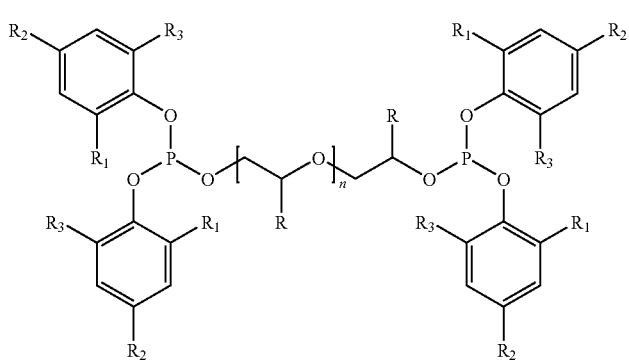
(I)

-continued

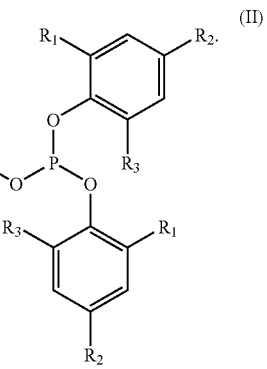

3. A mixture according to claim 1 comprising esters of formulae I and II

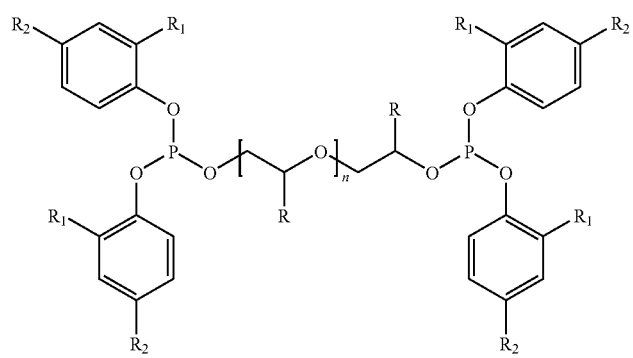

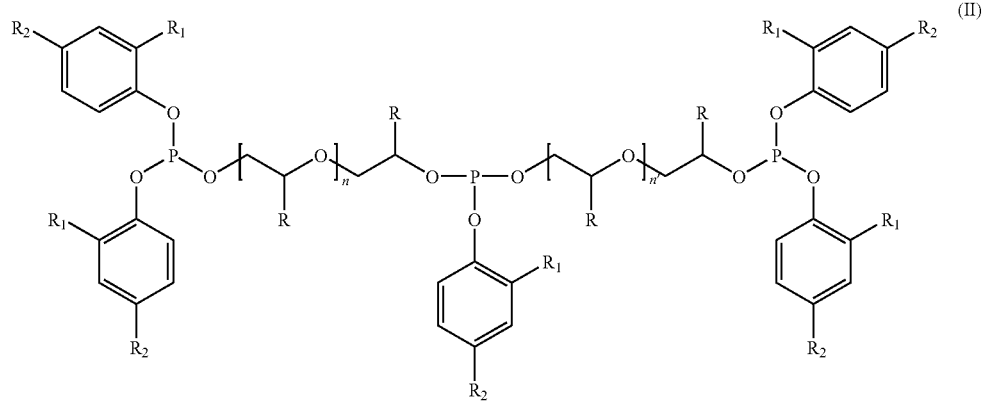

where
R$_1$ and R$_2$ are independently methyl, sec-butyl, tert-butyl, tert-octyl, α-cumyl, nonyl or methyl propanoate and
n and n' are independently from 2 to 30.

4. A mixture according to claim 3 where
R$_1$ and R$_2$ are independently sec-butyl or tert-butyl or methyl propanoate and
n and n' are independently from 2 to 5.

5. A mixture according to claim 3 where
R$_1$ and R$_2$ are independently sec-butyl or methyl propanoate and
n and n' are independently 2, 3 or 4.

6. A mixture according to claim 1 where the molar ratio of compounds of formula I to II is from about 1:9 to about 9:1.

7. A mixture according to claim 1 where the molar ratio of compounds of formula I to II is from about 1:3 to about 3:1.

8. A polyolefin composition stabilized against the deleterious effects of melt processing, heat aging and exposure to combustion products of natural gas, which composition comprises
a polyolefin substrate and incorporated therein
a mixture comprising oxyalkylene bridged bis- and trisphosphite esters of the formula I and II according to claim 1.

9. A composition according to claim 8 where the mixture of esters is present at a level of from about 0.01% to about 5% by weight, based on the weight of the polyolefin.

10. A composition according to claim 8 where the mixture of esters is present at a level of less than about 3% by weight, based on the weight of the polyolefin.

11. A composition according to claim 8 where one or more further stabilizers are present, the further stabilizers being selected from the group consisting of hindered phenolic antioxidants, hydroxylamines, benzofuranones, other organic phosphorus stabilizers, sterically hindered amine light stabilizers and hydroxyphenylbenzotriazole, tris-aryl-s-triazine or hydroxyphenylbenzophenone ultraviolet light absorbers.

12. A composition according to claim 8 further comprising a hindered amine light stabilizer or a hydroxylamine stabilizer.

13. A composition according to claim 8 where the polyolefin is polyethylene.

14. A composition according to claim 8 where the polyolefin is low density polyethylene.

15. A phosphite ester compound of the structure

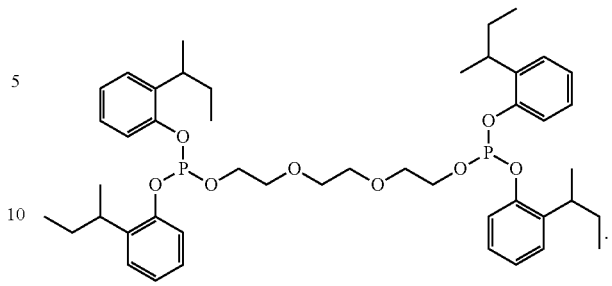

16. A phosphite ester compound of the structure

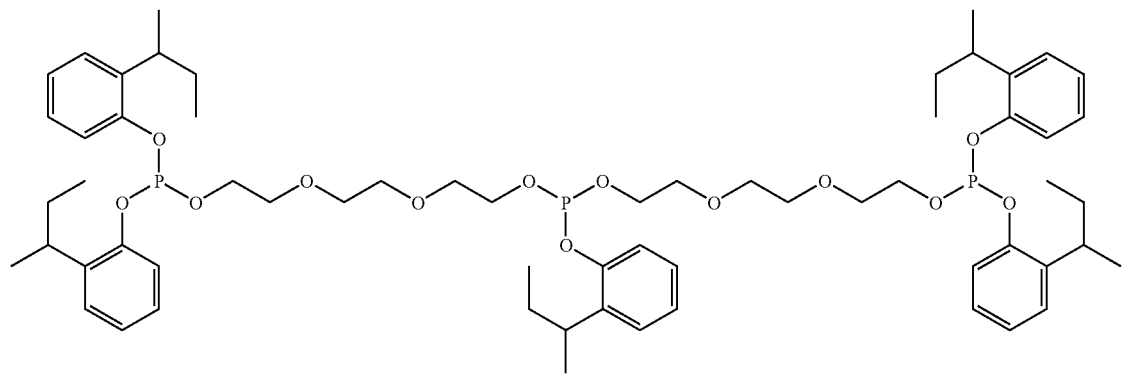

* * * * *